United States Patent
Ewers et al.

(10) Patent No.: US 8,496,581 B2
(45) Date of Patent: *Jul. 30, 2013

(54) SURGICAL ACCESS APPARATUS AND METHOD

(75) Inventors: Richard C. Ewers, Fullerton, CA (US); John R. Brustad, Dana Point, CA (US); Edward D. Pingleton, San Juan Capistrano, CA (US); Nabil Hilal, Laguna Niguel, CA (US); Gary R. Dulak, Valencia, CA (US); Payam Adlparvar, Lake Forest, CA (US); Robert R. Bowes, Laguna Hills, CA (US)

(73) Assignee: Applied Medical Resources Corporation, Rancho Santo Margarita, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 13/421,730

(22) Filed: Mar. 15, 2012

(65) Prior Publication Data
US 2012/0184821 A1    Jul. 19, 2012

Related U.S. Application Data

(63) Continuation of application No. 13/231,348, filed on Sep. 13, 2011, which is a continuation of application No. 12/960,458, filed on Dec. 3, 2010, now Pat. No. 8,016,755, which is a continuation of application No. 12/360,710, filed on Jan. 27, 2009, now Pat. No. 8,105,234, which is a continuation of application No. 11/244,647, filed on Oct. 5, 2005, now Pat. No. 7,481,765, which is a continuation of application No. 10/381,220, filed as application No. PCT/US01/29682 on Sep. 21, 2001, now Pat. No. 7,473,221.

(60) Provisional application No. 60/241,958, filed on Oct. 19, 2000.

(51) Int. Cl.
*A61B 1/32* (2006.01)

(52) U.S. Cl.
USPC ......................................................... 600/208

(58) Field of Classification Search
USPC ........................ 606/108, 191, 213, 205–207; 604/164.01–164.11, 165, 166, 167, 246, 604/247, 250, 264; 600/206, 208
See application file for complete search history.

(56) References Cited

U.S. PATENT DOCUMENTS

| 558,364 A | 4/1896 | Doolittle |
| 1,157,202 A | 10/1915 | Bates et al. |

(Continued)

FOREIGN PATENT DOCUMENTS

| DE | 26 05 148 | 8/1977 |
| DE | 33 36 279 | 1/1986 |

(Continued)

OTHER PUBLICATIONS

Foaming agent, Wikepedia on line, accessed on Dec. 26, 2012.*

(Continued)

*Primary Examiner* — Tuan V Nguyen
(74) *Attorney, Agent, or Firm* — Knobbe Martens Olson & Bear, LLP

(57) ABSTRACT

A device includes an access port adapted to permit access of at least one surgical instrument into a patient. The access port includes a proximal portion, a distal portion, and an intermediate portion monolithically formed of a flexible material. At least one opening extends through the access port. The proximal portion includes a proximal flange. The distal portion includes a distal flange. The intermediate portion includes an outer surface and at least one inner surface. The access port is adapted to form a perimeter seal when the proximal flange is disposed exteriorly and the distal flange is disposed interiorly. The access port is adapted to form a seal with the at least one surgical instrument positioned through the access port. The intermediate portion conforms to the surface of the surgical instrument positioned through the at least one opening and forms the seal between the inner surface and the surgical instrument.

23 Claims, 18 Drawing Sheets

U.S. PATENT DOCUMENTS

| | | | |
|---|---|---|---|
| 1,598,284 A | 8/1926 | Kinney | |
| 1,690,995 A | 11/1928 | Pratt | |
| 1,810,466 A | 6/1931 | Deutsch | |
| 2,219,564 A | 10/1940 | Reyniers | |
| 2,305,289 A | 12/1942 | Coburg | |
| 2,478,586 A | 8/1949 | Krapp | |
| 2,669,991 A | 2/1954 | Curutchet | |
| 2,695,608 A | 11/1954 | Gibbon | |
| 2,812,758 A | 11/1957 | Blumenschein | |
| 2,835,253 A | 5/1958 | Borgeson | |
| 2,853,075 A | 9/1958 | Hoffman et al. | |
| 3,039,468 A | 6/1962 | Price | |
| 3,057,350 A | 10/1962 | Cowley | |
| 3,111,943 A | 11/1963 | Orndorff | |
| 3,195,934 A | 7/1965 | Parrish | |
| 3,244,169 A | 4/1966 | Baxter | |
| 3,253,594 A | 5/1966 | Matthews et al. | |
| 3,313,299 A | 4/1967 | Spademan | |
| 3,329,390 A | 7/1967 | Hulsey | |
| 3,332,417 A | 7/1967 | Blanford et al. | |
| 3,347,226 A | 10/1967 | Harrower | |
| 3,347,227 A | 10/1967 | Harrower | |
| 3,397,692 A | 8/1968 | Creager, Jr. et al. | |
| 3,402,710 A | 9/1968 | Paleschuck | |
| 3,416,520 A | 12/1968 | Creager, Jr. | |
| 3,447,533 A | 6/1969 | Spicer | |
| 3,522,800 A | 8/1970 | Lesser | |
| 3,523,534 A | 8/1970 | Nolan | |
| 3,570,475 A | 3/1971 | Weinstein | |
| 3,656,485 A | 4/1972 | Robertson | |
| 3,685,786 A | 8/1972 | Woodson | |
| 3,717,151 A | 2/1973 | Collett | |
| 3,717,883 A | 2/1973 | Mosher | |
| 3,729,006 A | 4/1973 | Wilder et al. | |
| 3,782,370 A | 1/1974 | McDonald | |
| 3,797,478 A | 3/1974 | Walsh et al. | |
| 3,799,166 A | 3/1974 | Marsan | |
| 3,807,393 A | 4/1974 | McDonald | |
| 3,828,764 A | 8/1974 | Jones | |
| 3,831,583 A | 8/1974 | Edmunds et al. | |
| 3,841,332 A | 10/1974 | Treacle | |
| 3,850,172 A | 11/1974 | Cazalis | |
| 3,853,126 A | 12/1974 | Schulte | |
| 3,853,127 A | 12/1974 | Spademan | |
| 3,856,021 A | 12/1974 | McIntosh | |
| 3,860,274 A | 1/1975 | Ledstrom et al. | |
| 3,861,416 A | 1/1975 | Wichterle | |
| 3,907,389 A | 9/1975 | Cox et al. | |
| 3,915,171 A | 10/1975 | Shermeta | |
| 3,965,890 A | 6/1976 | Gauthier | |
| 3,970,089 A | 7/1976 | Saice | |
| 3,996,623 A | 12/1976 | Kaster | |
| 4,000,739 A | 1/1977 | Stevens | |
| 4,016,884 A * | 4/1977 | Kwan-Gett | 604/175 |
| 4,024,872 A | 5/1977 | Muldoon | |
| 4,030,500 A | 6/1977 | Ronnquist | |
| 4,043,328 A | 8/1977 | Cawood, Jr. et al. | |
| 4,069,913 A | 1/1978 | Harrigan | |
| 4,082,005 A | 4/1978 | Erdley | |
| 4,083,370 A | 4/1978 | Taylor | |
| 4,096,853 A | 6/1978 | Weigand | |
| 4,112,932 A | 9/1978 | Chiulli | |
| 4,130,113 A | 12/1978 | Graham | |
| 4,177,814 A | 12/1979 | Knepshield et al. | |
| 4,183,357 A | 1/1980 | Bentley et al. | |
| 4,187,849 A | 2/1980 | Stim | |
| 4,188,945 A | 2/1980 | Wenander | |
| 4,217,664 A | 8/1980 | Faso | |
| 4,222,126 A | 9/1980 | Boretos et al. | |
| 4,228,792 A | 10/1980 | Rhys-Davies | |
| 4,239,036 A | 12/1980 | Krieger | |
| 4,240,411 A | 12/1980 | Hosono | |
| 4,253,201 A | 3/1981 | Ross et al. | |
| 4,254,973 A | 3/1981 | Benjamin | |
| 4,306,562 A | 12/1981 | Osborne | |
| 4,321,915 A | 3/1982 | Leighton | |
| 4,331,138 A | 5/1982 | Jessen | |
| 4,338,934 A | 7/1982 | Spademan | |
| 4,338,937 A | 7/1982 | Lerman | |
| 4,367,728 A | 1/1983 | Mutke | |
| 4,369,284 A | 1/1983 | Chen | |
| 4,399,816 A | 8/1983 | Spangler | |
| 4,402,683 A | 9/1983 | Kopman | |
| 4,411,659 A | 10/1983 | Jensen et al. | |
| 4,421,296 A | 12/1983 | Stephens | |
| 4,424,833 A | 1/1984 | Spector et al. | |
| 4,428,364 A | 1/1984 | Bartolo | |
| 4,430,081 A | 2/1984 | Timmermans | |
| 4,434,791 A | 3/1984 | Darnell | |
| 4,436,519 A | 3/1984 | O'Neill | |
| 4,454,873 A | 6/1984 | Laufenberg et al. | |
| 4,473,067 A | 9/1984 | Schiff | |
| 4,475,548 A | 10/1984 | Muto | |
| 4,485,490 A | 12/1984 | Akers et al. | |
| 4,488,877 A | 12/1984 | Klein | |
| 4,496,349 A | 1/1985 | Cosentino | |
| 4,543,088 A | 9/1985 | Bootman et al. | |
| 4,550,713 A | 11/1985 | Hyman | |
| 4,553,537 A | 11/1985 | Rosenberg | |
| 4,555,242 A | 11/1985 | Saudagar | |
| 4,556,996 A | 12/1985 | Wallace | |
| 4,601,710 A | 7/1986 | Moll | |
| 4,610,665 A | 9/1986 | Matsumoto et al. | |
| 4,626,245 A | 12/1986 | Weinstein | |
| 4,634,424 A | 1/1987 | O'Boyle | |
| 4,634,432 A | 1/1987 | Kocak | |
| 4,644,951 A | 2/1987 | Bays | |
| 4,649,904 A | 3/1987 | Krauter | |
| 4,653,476 A | 3/1987 | Bonnet | |
| 4,654,030 A | 3/1987 | Moll et al. | |
| 4,655,752 A | 4/1987 | Honkanen et al. | |
| 4,673,393 A | 6/1987 | Suzuki et al. | |
| 4,673,394 A | 6/1987 | Fenton | |
| 4,691,942 A | 9/1987 | Ford | |
| 4,714,749 A | 12/1987 | Hughes et al. | |
| 4,738,666 A | 4/1988 | Fuqua | |
| 4,755,170 A | 7/1988 | Golden | |
| 4,760,933 A | 8/1988 | Christner et al. | |
| 4,776,843 A | 10/1988 | Martinez et al. | |
| 4,777,943 A | 10/1988 | Chvapil | |
| 4,784,646 A | 11/1988 | Feingold | |
| 4,796,629 A | 1/1989 | Grayzel | |
| 4,798,594 A | 1/1989 | Hillstead | |
| 4,802,694 A | 2/1989 | Vargo | |
| 4,808,168 A | 2/1989 | Warring | |
| 4,809,679 A | 3/1989 | Shimonaka et al. | |
| 4,828,554 A | 5/1989 | Griffin | |
| 4,842,931 A | 6/1989 | Zook | |
| 4,848,575 A | 7/1989 | Nakamura et al. | |
| 4,856,502 A | 8/1989 | Ersfeld et al. | |
| 4,863,430 A | 9/1989 | Klyce et al. | |
| 4,863,438 A | 9/1989 | Gauderer et al. | |
| 4,889,107 A | 12/1989 | Kaufman | |
| 4,895,565 A | 1/1990 | Hillstead | |
| 4,897,081 A | 1/1990 | Poirier | |
| 4,903,710 A | 2/1990 | Jessamine et al. | |
| 4,911,974 A | 3/1990 | Shimizu et al. | |
| 4,915,132 A | 4/1990 | Hodge et al. | |
| 4,926,882 A | 5/1990 | Lawrence | |
| 4,929,235 A | 5/1990 | Merry et al. | |
| 4,944,732 A | 7/1990 | Russo | |
| 4,950,222 A | 8/1990 | Scott et al. | |
| 4,950,223 A | 8/1990 | Silvanov | |
| 4,984,564 A | 1/1991 | Yuen | |
| 4,991,593 A | 2/1991 | LeVahn | |
| 4,998,538 A | 3/1991 | Charowsky et al. | |
| 5,000,745 A | 3/1991 | Guest et al. | |
| 5,009,224 A | 4/1991 | Cole | |
| 5,015,228 A | 5/1991 | Columbus et al. | |
| 5,019,101 A | 5/1991 | Purkait et al. | |
| 5,026,366 A | 6/1991 | Leckrone | |
| 5,037,379 A | 8/1991 | Clayman et al. | |
| 5,041,095 A | 8/1991 | Littrell | |
| 5,045,070 A | 9/1991 | Grodecki et al. | |
| D320,658 S | 10/1991 | Quigley et al. | |
| 5,071,411 A | 12/1991 | Hillstead | |
| 5,073,169 A | 12/1991 | Raiken | |

| Patent No. | Kind | Date | Inventor(s) |
|---|---|---|---|
| 5,074,878 | A | 12/1991 | Bark et al. |
| 5,082,005 | A | 1/1992 | Kaldany |
| 5,086,763 | A | 2/1992 | Hathman |
| 5,092,846 | A | 3/1992 | Nishijima et al. |
| 5,104,389 | A | 4/1992 | Deem |
| 5,125,396 | A | 6/1992 | Ray |
| 5,125,897 | A | 6/1992 | Quinn et al. |
| 5,127,626 | A | 7/1992 | Hilal et al. |
| 5,129,885 | A | 7/1992 | Green et al. |
| 5,141,498 | A | 8/1992 | Christian |
| 5,149,327 | A | 9/1992 | Oshiyama |
| 5,156,617 | A | 10/1992 | Reid |
| 5,158,553 | A | 10/1992 | Berry et al. |
| 5,159,921 | A | 11/1992 | Hoover |
| 5,161,773 | A | 11/1992 | Tower |
| 5,167,636 | A | 12/1992 | Clement |
| 5,167,637 | A | 12/1992 | Okada et al. |
| 5,176,648 | A | 1/1993 | Holmes et al. |
| 5,176,662 | A | 1/1993 | Bartholomew et al. |
| 5,176,697 | A | 1/1993 | Hasson et al. |
| 5,178,162 | A | 1/1993 | Bose |
| 5,180,365 | A | 1/1993 | Ensminger et al. |
| 5,183,471 | A | 2/1993 | Wilk |
| 5,188,595 | A | 2/1993 | Jacobi |
| 5,188,607 | A | 2/1993 | Wu |
| 5,192,301 | A | 3/1993 | Kamiya et al. |
| 5,197,955 | A | 3/1993 | Stephens et al. |
| 5,207,656 | A | 5/1993 | Kranys |
| 5,209,737 | A | 5/1993 | Rirchart et al. |
| 5,211,370 | A | 5/1993 | Powers |
| 5,211,633 | A | 5/1993 | Stouder, Jr. |
| 5,213,114 | A | 5/1993 | Bailey, Jr. |
| 5,226,890 | A | 7/1993 | Ianniruberto et al. |
| 5,234,455 | A | 8/1993 | Mulhollan |
| 5,241,968 | A | 9/1993 | Slater |
| 5,242,409 | A | 9/1993 | Buelna |
| 5,242,412 | A | 9/1993 | Blake, III |
| 5,242,415 | A | 9/1993 | Kantrowitz et al. |
| 5,248,304 | A | 9/1993 | Vigdorchik et al. |
| 5,256,150 | A | 10/1993 | Quiachon et al. |
| 5,257,973 | A | 11/1993 | Villasuso |
| 5,257,975 | A | 11/1993 | Foshee |
| 5,259,366 | A | 11/1993 | Reydel et al. |
| 5,261,883 | A | 11/1993 | Hood et al. |
| 5,262,468 | A | 11/1993 | Chen |
| 5,263,922 | A | 11/1993 | Sova et al. |
| 5,269,763 | A | 12/1993 | Boehmer et al. |
| 5,269,772 | A | 12/1993 | Wilk |
| 5,273,449 | A | 12/1993 | Mattis et al. |
| 5,273,545 | A | 12/1993 | Hunt et al. |
| D343,236 | S | 1/1994 | Quigley et al. |
| 5,279,575 | A | 1/1994 | Sugarbaker |
| 5,290,310 | A | 3/1994 | Makower et al. |
| D346,022 | S | 4/1994 | Quigley et al. |
| 5,299,582 | A | 4/1994 | Potts |
| 5,300,033 | A | 4/1994 | Miller |
| 5,300,034 | A | 4/1994 | Behnke |
| 5,300,035 | A | 4/1994 | Clement |
| 5,300,036 | A | 4/1994 | Mueller et al. |
| 5,308,336 | A | 5/1994 | Hart et al. |
| 5,309,896 | A | 5/1994 | Moll et al. |
| 5,312,391 | A | 5/1994 | Wilk |
| 5,314,417 | A | 5/1994 | Stephens et al. |
| 5,316,541 | A | 5/1994 | Fischer |
| 5,320,611 | A | 6/1994 | Bonutti et al. |
| 5,330,437 | A | 7/1994 | Durman |
| 5,330,486 | A | 7/1994 | Wilk |
| 5,330,497 | A | 7/1994 | Freitas et al. |
| 5,331,975 | A | 7/1994 | Bonutti |
| 5,334,143 | A | 8/1994 | Carroll |
| 5,334,646 | A | 8/1994 | Chen |
| 5,336,192 | A | 8/1994 | Palestrant |
| 5,336,708 | A | 8/1994 | Chen |
| 5,338,313 | A | 8/1994 | Mollenauer et al. |
| 5,342,315 | A | 8/1994 | Rowe et al. |
| 5,342,385 | A | 8/1994 | Norelli et al. |
| 5,350,364 | A | 9/1994 | Stephens et al. |
| 5,353,786 | A | 10/1994 | Wilk |
| 5,354,280 | A | 10/1994 | Haber et al. |
| 5,360,417 | A | 11/1994 | Gravener et al. |
| 5,364,345 | A | 11/1994 | Lowery et al. |
| 5,364,372 | A | 11/1994 | Danks et al. |
| 5,366,446 | A | 11/1994 | Tal et al. |
| 5,366,478 | A | 11/1994 | Brinkerhoff et al. |
| 5,368,545 | A | 11/1994 | Schaller et al. |
| 5,375,588 | A | 12/1994 | Yoon |
| 5,380,288 | A | 1/1995 | Hart et al. |
| 5,380,302 | A | 1/1995 | Orth |
| 5,383,861 | A | 1/1995 | Hempel et al. |
| 5,385,552 | A | 1/1995 | Haber et al. |
| 5,385,553 | A | 1/1995 | Hart et al. |
| 5,385,560 | A | 1/1995 | Wulf |
| 5,389,080 | A | 2/1995 | Yoon |
| 5,389,081 | A | 2/1995 | Castro |
| 5,391,153 | A | 2/1995 | Haber et al. |
| 5,391,156 | A | 2/1995 | Hildwein et al. |
| 5,395,367 | A | 3/1995 | Wilk |
| 5,403,264 | A | 4/1995 | Wohlers et al. |
| 5,403,336 | A | 4/1995 | Kieturakis et al. |
| 5,407,433 | A | 4/1995 | Loomas |
| 5,411,483 | A | 5/1995 | Loomas |
| 5,413,571 | A | 5/1995 | Katsaros et al. |
| 5,423,848 | A | 6/1995 | Washizuka et al. |
| 5,429,609 | A | 7/1995 | Yoon |
| 5,431,676 | A | 7/1995 | Dubrul et al. |
| 5,437,683 | A | 8/1995 | Neumann et al. |
| 5,439,455 | A | 8/1995 | Kieturakis et al. |
| 5,441,486 | A | 8/1995 | Yoon |
| 5,443,452 | A | 8/1995 | Hart et al. |
| 5,456,284 | A | 10/1995 | Ryan et al. |
| 5,460,170 | A | 10/1995 | Hammerslag |
| 5,460,616 | A | 10/1995 | Weinstein et al. |
| 5,468,248 | A | 11/1995 | Chin et al. |
| 5,476,475 | A | 12/1995 | Gadberry |
| 5,480,410 | A | 1/1996 | Cuschieri et al. |
| 5,486,426 | A | 1/1996 | McGee et al. |
| 5,490,843 | A | 2/1996 | Hildwein et al. |
| 5,492,304 | A | 2/1996 | Smith et al. |
| 5,496,280 | A | 3/1996 | Vandenbroek et al. |
| 5,503,112 | A | 4/1996 | Luhman et al. |
| 5,507,758 | A | 4/1996 | Thomason et al. |
| 5,508,334 | A | 4/1996 | Chen |
| 5,511,564 | A | 4/1996 | Wilk |
| 5,514,109 | A | 5/1996 | Mollenauer et al. |
| 5,514,133 | A | 5/1996 | Golub et al. |
| 5,514,153 | A | 5/1996 | Bonutti |
| 5,518,278 | A | 5/1996 | Sampson |
| 5,520,632 | A | 5/1996 | Leveen |
| 5,522,791 | A | 6/1996 | Leyva |
| 5,522,824 | A | 6/1996 | Ashby |
| 5,524,644 | A | 6/1996 | Crook |
| 5,526,536 | A | 6/1996 | Cartmill |
| 5,531,758 | A | 7/1996 | Uschold et al. |
| 5,538,509 | A | 7/1996 | Dunlap et al. |
| 5,540,648 | A | 7/1996 | Yoon |
| 5,540,711 | A | 7/1996 | Kieturakis et al. |
| 5,545,150 | A | 8/1996 | Danks et al. |
| 5,545,179 | A | 8/1996 | Williamson, IV |
| 5,549,563 | A | 8/1996 | Kronner |
| 5,549,637 | A | 8/1996 | Crainich |
| 5,554,124 | A | 9/1996 | Alvarado |
| 5,562,632 | A | 10/1996 | Davila et al. |
| 5,562,677 | A | 10/1996 | Hildwein et al. |
| 5,562,688 | A | 10/1996 | Riza |
| 5,571,115 | A | 11/1996 | Nicholas |
| 5,571,137 | A | 11/1996 | Marlow et al. |
| 5,575,799 | A | 11/1996 | Bolanos et al. |
| 5,577,993 | A | 11/1996 | Zhu et al. |
| 5,578,048 | A | 11/1996 | Pasqualucci et al. |
| 5,580,344 | A | 12/1996 | Hasson |
| 5,584,850 | A | 12/1996 | Hart et al. |
| 5,601,579 | A | 2/1997 | Semertzides |
| 5,601,581 | A | 2/1997 | Fogarty et al. |
| 5,603,702 | A | 2/1997 | Smith et al. |
| 5,607,443 | A | 3/1997 | Kieturakis et al. |
| 5,620,415 | A | 4/1997 | Lucey et al. |
| 5,620,420 | A | 4/1997 | Kriesel |
| 5,628,732 | A | 5/1997 | Antoon, Jr. et al. |

| | | | | | | |
|---|---|---|---|---|---|---|
| 5,632,284 A | 5/1997 | Graether | | 5,899,208 A | 5/1999 | Bonadio |
| 5,632,979 A | 5/1997 | Goldberg et al. | | 5,899,913 A | 5/1999 | Fogarty et al. |
| 5,634,911 A | 6/1997 | Hermann et al. | | 5,904,703 A | 5/1999 | Gilson |
| 5,634,936 A | 6/1997 | Linden et al. | | 5,906,577 A | 5/1999 | Beane et al. |
| 5,634,937 A | 6/1997 | Mollenauer et al. | | 5,913,847 A | 6/1999 | Yoon |
| 5,636,645 A | 6/1997 | Ou | | 5,916,198 A | 6/1999 | Dillow |
| 5,640,977 A | 6/1997 | Leahy et al. | | 5,916,232 A | 6/1999 | Hart |
| 5,643,301 A | 7/1997 | Mollenauer | | 5,919,476 A | 7/1999 | Fischer et al. |
| 5,649,550 A | 7/1997 | Crook | | 5,931,832 A | 8/1999 | Jensen |
| 5,651,771 A | 7/1997 | Tangherlini et al. | | 5,947,922 A | 9/1999 | MacLeod |
| 5,653,705 A | 8/1997 | de la Torre et al. | | 5,951,467 A | 9/1999 | Picha et al. |
| 5,657,963 A | 8/1997 | Hinchliffe et al. | | 5,951,588 A | 9/1999 | Moenning |
| 5,658,272 A | 8/1997 | Hasson | | 5,957,888 A | 9/1999 | Hinchiffe et al. |
| 5,658,306 A | 8/1997 | Kieturakis et al. | | 5,957,913 A | 9/1999 | de la Torre et al. |
| 5,662,615 A | 9/1997 | Blake, III | | 5,962,572 A | 10/1999 | Chen |
| 5,672,168 A | 9/1997 | de la Torre et al. | | 5,964,781 A | 10/1999 | Mollenauer et al. |
| 5,681,341 A | 10/1997 | Lunsford et al. | | 5,976,174 A | 11/1999 | Ruiz |
| 5,683,378 A | 11/1997 | Christy | | 5,989,232 A | 11/1999 | Yoon |
| 5,685,854 A | 11/1997 | Green et al. | | 5,989,233 A | 11/1999 | Yoon |
| 5,685,857 A | 11/1997 | Negus et al. | | 5,989,266 A | 11/1999 | Foster |
| 5,697,914 A | 12/1997 | Brimhall | | 5,993,471 A | 11/1999 | Riza et al. |
| 5,707,703 A | 1/1998 | Rothrum et al. | | 5,993,485 A | 11/1999 | Beckers |
| 5,709,664 A | 1/1998 | Vandenbroek et al. | | 5,994,450 A | 11/1999 | Pearce |
| 5,713,858 A | 2/1998 | Heruth et al. | | 5,997,515 A | 12/1999 | de la Torre et al. |
| 5,713,869 A | 2/1998 | Morejon | | 6,004,303 A | 12/1999 | Peterson |
| 5,720,730 A | 2/1998 | Blake, III | | 6,010,494 A | 1/2000 | Schafer et al. |
| 5,725,536 A | 3/1998 | Oberlin et al. | | 6,017,355 A | 1/2000 | Hessel et al. |
| 5,728,103 A * | 3/1998 | Picha et al. ............ 606/108 | | 6,018,094 A | 1/2000 | Fox |
| 5,730,748 A | 3/1998 | Fogarty et al. | | 6,024,736 A | 2/2000 | de la Torre et al. |
| 5,735,791 A | 4/1998 | Alexander et al. | | 6,025,067 A | 2/2000 | Fay |
| 5,738,628 A | 4/1998 | Sierocuk et al. | | 6,033,426 A | 3/2000 | Kaji |
| 5,741,234 A | 4/1998 | Aboul-Hosn | | 6,033,428 A | 3/2000 | Sardella |
| 5,741,298 A | 4/1998 | MacLeod | | 6,035,559 A | 3/2000 | Freed et al. |
| 5,743,884 A | 4/1998 | Hasson et al. | | 6,042,573 A | 3/2000 | Lucey |
| 5,749,882 A | 5/1998 | Hart et al. | | 6,045,535 A | 4/2000 | Ben Nun |
| 5,755,660 A | 5/1998 | Tyagi | | 6,048,309 A | 4/2000 | Flom et al. |
| 5,760,117 A | 6/1998 | Chen | | 6,050,871 A | 4/2000 | Chen |
| 5,769,783 A | 6/1998 | Fowler | | 6,053,934 A | 4/2000 | Andrews et al. |
| 5,782,812 A | 7/1998 | Hart et al. | | 6,059,816 A | 5/2000 | Moenning |
| 5,782,817 A | 7/1998 | Franzel et al. | | 6,066,117 A | 5/2000 | Fox et al. |
| 5,782,859 A | 7/1998 | Nicholas et al. | | 6,068,639 A | 5/2000 | Fogarty et al. |
| 5,788,676 A | 8/1998 | Yoon | | 6,077,288 A | 6/2000 | Shimomura et al. |
| 5,792,119 A | 8/1998 | Marx | | 6,086,603 A | 7/2000 | Termin et al. |
| 5,795,290 A | 8/1998 | Bridges | | 6,090,043 A | 7/2000 | Austin et al. |
| 5,803,919 A | 9/1998 | Hart et al. | | 6,099,506 A * | 8/2000 | Macoviak et al. ........... 604/173 |
| 5,803,921 A | 9/1998 | Bonadio | | 6,110,154 A | 8/2000 | Shimomura et al. |
| 5,803,923 A | 9/1998 | Singh-Derewa et al. | | 6,123,689 A | 9/2000 | To et al. |
| 5,807,350 A | 9/1998 | Diaz | | 6,142,935 A | 11/2000 | Flom et al. |
| 5,810,712 A | 9/1998 | Dunn | | 6,142,936 A | 11/2000 | Beane et al. |
| 5,810,721 A | 9/1998 | Mueller et al. | | 6,149,642 A | 11/2000 | Gerhart et al. |
| 5,813,409 A | 9/1998 | Leahy et al. | | 6,150,608 A | 11/2000 | Wambeke et al. |
| 5,814,026 A | 9/1998 | Yoon | | 6,159,182 A | 12/2000 | Davis et al. |
| 5,817,062 A | 10/1998 | Flom et al. | | 6,162,172 A | 12/2000 | Cosgrove et al. |
| 5,819,375 A | 10/1998 | Kastner | | 6,162,196 A | 12/2000 | Hart et al. |
| 5,820,555 A | 10/1998 | Watkins, III et al. | | 6,162,206 A | 12/2000 | Bindokas et al. |
| 5,820,600 A | 10/1998 | Carlson et al. | | 6,163,949 A | 12/2000 | Neuenschwander |
| 5,830,191 A | 11/1998 | Hildwein et al. | | 6,164,279 A | 12/2000 | Tweedle |
| 5,832,925 A | 11/1998 | Rothrum | | 6,171,282 B1 | 1/2001 | Ragsdale |
| 5,836,871 A | 11/1998 | Wallace et al. | | 6,183,486 B1 | 2/2001 | Snow et al. |
| 5,841,298 A | 11/1998 | Huang | | 6,197,002 B1 | 3/2001 | Peterson |
| 5,842,971 A | 12/1998 | Yoon | | 6,217,555 B1 | 4/2001 | Hart et al. |
| 5,848,992 A | 12/1998 | Hart et al. | | 6,217,590 B1 | 4/2001 | Levinson |
| 5,853,395 A | 12/1998 | Crook et al. | | 6,224,612 B1 | 5/2001 | Bates et al. |
| 5,853,417 A | 12/1998 | Fogarty et al. | | 6,228,063 B1 | 5/2001 | Aboul-Hosn |
| 5,857,461 A | 1/1999 | Levitsky et al. | | 6,238,373 B1 | 5/2001 | de la Torre et al. |
| 5,860,995 A | 1/1999 | Berkelaar | | 6,241,768 B1 | 6/2001 | Agarwal et al. |
| 5,863,366 A | 1/1999 | Snow | | 6,254,533 B1 | 7/2001 | Fadem et al. |
| 5,865,728 A | 2/1999 | Moll et al. | | 6,254,534 B1 | 7/2001 | Butler et al. |
| 5,865,729 A | 2/1999 | Meehan et al. | | 6,258,065 B1 | 7/2001 | Dennis et al. |
| 5,865,807 A | 2/1999 | Blake, III | | 6,264,604 B1 | 7/2001 | Kieturakis et al. |
| 5,865,817 A | 2/1999 | Moenning et al. | | 6,267,751 B1 | 7/2001 | Mangosong |
| 5,871,474 A | 2/1999 | Hermann et al. | | 6,276,661 B1 | 8/2001 | Laird |
| 5,876,413 A | 3/1999 | Fogarty et al. | | 6,287,280 B1 | 9/2001 | Lampropoulos et al. |
| 5,879,290 A * | 3/1999 | Bridges et al. ............ 600/206 | | 6,315,770 B1 | 11/2001 | de la Torre et al. |
| 5,879,368 A | 3/1999 | Hoskin et al. | | 6,319,246 B1 | 11/2001 | de la Torre et al. |
| 5,882,344 A | 3/1999 | Stouder, Jr. | | 6,322,541 B2 | 11/2001 | West |
| 5,884,639 A | 3/1999 | Chen | | 6,325,384 B1 | 12/2001 | Berry, Sr. et al. |
| 5,894,843 A | 4/1999 | Benetti et al. | | 6,333,374 B1 | 12/2001 | Chen |
| 5,895,377 A | 4/1999 | Smith et al. | | 6,346,074 B1 | 2/2002 | Roth |

| | | |
|---|---|---|
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,416,499 B2 | 7/2002 | Paul, Jr. |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Lui et al. |
| 7,105,009 B2 | 9/2006 | Johnson et al. |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson et al. |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |

| Patent No. | Date | Inventor |
|---|---|---|
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,841,765 B2 | 11/2010 | Keller |
| 7,850,667 B2 | 12/2010 | Gresham |
| 7,867,164 B2 | 1/2011 | Butler et al. |
| 7,878,974 B2 | 2/2011 | Brustad et al. |
| 7,883,461 B2 | 2/2011 | Albrecht et al. |
| 7,892,172 B2 | 2/2011 | Albrecht et al. |
| 7,896,889 B2 | 3/2011 | Mazzocchi et al. |
| 7,909,760 B2 | 3/2011 | Albrecht et al. |
| 7,913,697 B2 | 3/2011 | Nguyen et al. |
| 7,930,782 B2 | 4/2011 | Chen |
| RE42,379 E | 5/2011 | Loomas |
| 7,951,076 B2 | 5/2011 | Hart et al. |
| 7,998,068 B2 | 8/2011 | Bonadio et al. |
| 8,016,755 B2 | 9/2011 | Ewers et al. |
| 8,021,296 B2 | 9/2011 | Bonadio et al. |
| 8,070,676 B2 | 12/2011 | Ewers et al. |
| 8,105,234 B2 | 1/2012 | Ewers et al. |
| 8,109,873 B2 | 2/2012 | Albrecht et al. |
| 8,114,111 B2 | 2/2012 | Piskun |
| 8,187,177 B2 | 5/2012 | Kahle et al. |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0049276 A1 | 4/2002 | Zwick |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson et al. |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkler, II et al. |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0187079 A1 | 7/2009 | Albrecht et al. |

| | | | | | | |
|---|---|---|---|---|---|---|
| 2009/0227843 A1 | 9/2009 | Smith et al. | | JP | 10-108868 | 4/1998 |
| 2009/0292176 A1 | 11/2009 | Bonadio et al. | | JP | 11-290327 | 10/1999 |
| 2009/0326330 A1 | 12/2009 | Bonadio et al. | | JP | 2001-61850 | 3/2001 |
| 2010/0063362 A1 | 3/2010 | Bonadio et al. | | JP | 2002-28163 | 1/2002 |
| 2010/0063364 A1 | 3/2010 | Bonadio et al. | | JP | 02003 235879 A | 8/2003 |
| 2010/0081880 A1 | 4/2010 | Widenhouse et al. | | JP | 2004-195037 | 7/2004 |
| 2010/0081881 A1 | 4/2010 | Murray et al. | | SU | 1342485 | 1/1997 |
| 2010/0081995 A1 | 4/2010 | Widenhouse et al. | | WO | WO 86/06272 | 11/1986 |
| 2010/0100043 A1 | 4/2010 | Racenet | | WO | WO 86/06316 | 11/1986 |
| 2010/0113882 A1 | 5/2010 | Widenhouse et al. | | WO | WO 92/11880 | 7/1992 |
| 2010/0217087 A1 | 8/2010 | Bonadio et al. | | WO | WO 92/21292 | 12/1992 |
| 2010/0228091 A1 | 9/2010 | Widenhouse et al. | | WO | WO 93/05740 | 4/1993 |
| 2010/0228092 A1 | 9/2010 | Ortiz et al. | | WO | WO 93/14801 | 8/1993 |
| 2010/0228094 A1 | 9/2010 | Ortiz et al. | | WO | WO 94/04067 | 3/1994 |
| 2010/0240960 A1 | 9/2010 | Richard | | WO | WO 94/22357 | 10/1994 |
| 2010/0249523 A1 | 9/2010 | Spiegal et al. | | WO | WO 95/05207 | 2/1995 |
| 2010/0249524 A1 | 9/2010 | Ransden et al. | | WO | WO 95/07056 | 3/1995 |
| 2010/0249525 A1 | 9/2010 | Shelton, IV et al. | | WO | WO 95/22289 | 8/1995 |
| 2010/0249694 A1 | 9/2010 | Choi et al. | | WO | WO 95/24864 | 9/1995 |
| 2010/0261972 A1 | 10/2010 | Widenhouse et al. | | WO | WO 95/27445 | 10/1995 |
| 2010/0261975 A1 | 10/2010 | Huey et al. | | WO | WO 95/27468 | 10/1995 |
| 2010/0286484 A1 | 11/2010 | Stellon et al. | | WO | WO 96/36283 | 11/1996 |
| 2010/0298646 A1 | 11/2010 | Stellon et al. | | WO | WO 97/11642 | 4/1997 |
| 2011/0021877 A1 | 1/2011 | Fortier et al. | | WO | WO 97/32514 | 9/1997 |
| 2011/0028891 A1 | 2/2011 | Okoniewski | | WO | WO 97/32515 | 9/1997 |
| 2011/0034935 A1 | 2/2011 | Kleyman | | WO | WO 97/42889 | 11/1997 |
| 2011/0034946 A1 | 2/2011 | Kleyman | | WO | WO 98/19853 | 5/1998 |
| 2011/0034947 A1 | 2/2011 | Kleyman | | WO | WO 98/35614 | 8/1998 |
| 2011/0071462 A1 | 3/2011 | Ewers et al. | | WO | WO 98/48724 | 11/1998 |
| 2011/0071463 A1 | 3/2011 | Ewers et al. | | WO | WO 99/03416 | 1/1999 |
| | | | | WO | WO 99/15068 | 4/1999 |
| FOREIGN PATENT DOCUMENTS | | | | WO | WO 99/16368 | 4/1999 |
| DE | 37 39 532 | 12/1988 | | WO | WO 99/22804 | 5/1999 |
| DE | 37 37 121 | 5/1989 | | WO | WO 99/25268 | 5/1999 |
| DE | 296 00 939 | 6/1996 | | WO | WO 99/29250 | 6/1999 |
| DE | 19828009 | 12/1999 | | WO | WO 00/32116 | 6/2000 |
| EP | 0113520 | 7/1984 | | WO | WO 00/32117 | 6/2000 |
| EP | 0142262 | 5/1985 | | WO | WO 00/32119 | 6/2000 |
| EP | 0 517 248 | 12/1992 | | WO | WO 00/32120 | 6/2000 |
| EP | 0537768 | 4/1993 | | WO | WO 00/35356 | 6/2000 |
| EP | 0 807 416 | 11/1997 | | WO | WO 00/54675 | 9/2000 |
| EP | 0 849 517 | 6/1998 | | WO | WO 00/54676 | 9/2000 |
| EP | 0950376 | 10/1999 | | WO | WO 00/54677 | 9/2000 |
| EP | 1118657 | 7/2001 | | WO | WO 01/08563 | 2/2001 |
| EP | 1 125 552 | 8/2001 | | WO | WO 01/08581 | 2/2001 |
| EP | 1312318 | 5/2003 | | WO | WO 01/26558 | 4/2001 |
| EP | 1 407 715 | 4/2004 | | WO | WO 01/26559 | 4/2001 |
| EP | 2044889 | 4/2009 | | WO | WO 01/45568 | 6/2001 |
| EP | 2 340 792 | 7/2011 | | WO | WO 01/49363 | 7/2001 |
| FR | 1456623 | 9/1966 | | WO | WO 01/91652 | 12/2001 |
| GB | 1151993 | 5/1969 | | WO | WO 02/07611 | 1/2002 |
| GB | 1355611 | 6/1974 | | WO | WO 02/17800 | 3/2002 |
| GB | 1372491 | 10/1974 | | WO | WO 02/34108 | 5/2002 |
| GB | 1379772 | 1/1975 | | WO | WO 03/011153 | 2/2003 |
| GB | 1400808 | 7/1975 | | WO | WO 03/011551 | 2/2003 |
| GB | 1407023 | 9/1975 | | WO | WO 03/026512 | 4/2003 |
| GB | 1482857 | 8/1977 | | WO | WO 03/032819 | 4/2003 |
| GB | 1496696 | 12/1977 | | WO | WO 03/034908 | 5/2003 |
| GB | 2071502 | 9/1981 | | WO | WO 03/061480 | 7/2003 |
| GB | 2255019 | 10/1992 | | WO | WO 03/077726 | 9/2003 |
| GB | 2275420 | 8/1994 | | WO | WO 03/103548 | 12/2003 |
| GB | 2298906 | 9/1996 | | WO | WO 2004/026153 | 4/2004 |
| IE | 930649 | 9/1993 | | WO | WO 2004/030547 | 4/2004 |
| IE | 930650 | 9/1993 | | WO | WO 2004/075730 | 9/2004 |
| IE | S940150 | 2/1994 | | WO | WO 2004/075741 | 9/2004 |
| IE | S940613 | 8/1994 | | WO | WO 2004/075930 | 9/2004 |
| IE | S940960 | 12/1994 | | WO | WO 2005/009257 | 2/2005 |
| IE | S950055 | 1/1995 | | WO | WO 2005/034766 | 4/2005 |
| IE | S950266 | 4/1995 | | WO | WO 2005/089661 | 9/2005 |
| IE | S75368 | 8/1997 | | WO | WO 2006/040748 | 4/2006 |
| IE | S960196 | 8/1997 | | WO | WO 2006/059318 | 6/2006 |
| IE | S970810 | 11/1997 | | WO | WO 2006/100658 | 9/2006 |
| IE | 991010 | 7/2000 | | WO | WO 2007/044849 | 4/2007 |
| IE | 990218 | 11/2000 | | WO | WO 2008/015566 | 2/2008 |
| IE | 990219 | 11/2000 | | WO | WO 2008/093313 | 8/2008 |
| IE | 990220 | 11/2000 | | WO | WO 2008/121294 | 10/2008 |
| IE | 990660 | 2/2001 | | WO | WO 2010/082722 | 7/2010 |
| IE | 990795 | 3/2001 | | WO | WO 2010/104259 | 9/2010 |
| JP | H10-66697 | 3/1998 | | | | |

OTHER PUBLICATIONS

U.S. Appl. No. 10/381,220, filed Mar. 20, 2003; Title: Surgical Access Apparatus and Method, now USPN 7,473,221 issued Jan. 6, 2009.
U.S. Appl. No. 10/436,522, filed May 13, 2003; Title: Laparoscopic Illumination Apparatus and Method, now USPN 6,939,296 issued Sep. 6, 2005.
U.S. Appl. No. 10/399,209, filed Aug. 22, 2003; Title: Wound Retraction Apparatus and Method, now USPN 6,958,037 issued Oct. 25, 2005.
U.S. Appl. No. 11/218,412, filed Sep. 1, 2005; Title: Wound Retraction Apparatus and Method, now USPN 7,238,154 issued Jul. 3, 2007.
U.S. Appl. No. 10/399,057, filed Apr. 11, 2003; Title: Sealed Surgical Access Device, now USPN 7,052,454 issued May 30, 2006.
U.S. Appl. No. 10/666,579, filed Sep. 17, 2003; Title: Surgical Instrument Access Device, now USPN 7,163,510 issued Jan. 16, 2007.
U.S. Appl. No. 10/052,297, filed Jan. 18, 2002; Title: Hand Access Port Device, now USPN 6,908,430 issued Jun. 21, 2005.
U.S. Appl. No. 08/015,765, filed Feb. 10, 1993; Title: Gas-Tight Seal Accomodating Surgical Instruments With a Wide Range of Diameters, now USPN 5,407,433 issued Apr. 18, 1995.
U.S. Appl. No. 08/040,373, filed Mar. 30, 1993; Title: Gas-Tight Seal Accomodating Surgical Instruments With a Wide Range of Diameters, now USPN 5,411,483 issued May 2, 1995.
U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/516,198, filed Nov. 30, 2004; Title: Wound Retractor, now USPN 7,650,887 issued Jan. 26, 2010.
U.S. Appl. No. 10/927,551, filed Aug. 25, 2004; Title: Surgical Access System, now abandoned.
U.S. Appl. No. 11/244,647, filed Oct. 5, 2005; Title: Surgical Access Apparatus and Method, now USPN 7,481,765 issued Jan. 27, 2009.
U.S. Appl. No. 11/548,746, filed Oct. 12, 2006; Title: Method of Making a Hand Access Laparoscopic Device, now USPN 7,749,415 issued Jul. 6, 2010.
U.S. Appl. No. 11/548,765, filed Oct. 12, 2006; Title: Split Hoop Wound Retractor, now USPN 7,815,567 issued Oct. 26, 2010.
U.S. Appl. No. 11/548,767, filed Oct. 12, 2006; Title: Circular Surgical Retractor now USPN 7,704,207 issued Apr. 27, 2010.
U.S. Appl. No. 11/548,781, filed Oct. 12, 2006; Title: Wound Retractor With Gel Cap, now USPN 7,727,146 issued Jun. 1, 2010.
U.S. Appl. No. 11/548,955, filed Oct. 12, 2006; Title: Hand Access Laparoscopic Device, now USPN 7,736,306 issued Jun. 15, 2010.
U.S. Appl. No. 11/755,305, filed May 30, 2007; Title: Wound Retraction Apparatus and Method, now USPN 7,377,898 issued May 27, 2008.
U.S. Appl. No. 11/548,758, filed Oct. 12, 2007; Title: Split Hoop Wound Retractor With Gel Pad, now USPN 7,909,760 issued Mar. 22, 2011.
U.S. Appl. No. 12/693,242, filed Jan. 1, 2010; Title: Wound Retractor, now USPN 7,913,697 issued Mar. 29, 2011.
U.S. Appl. No. 12/768,328, filed Apr. 27, 2010; Title: Circular Surgical Retractor, now USPN 7,892,172 issued Feb. 22, 2011.
U.S. Appl. No. 12/791,666, filed Jun. 1, 2010; Title: Wound Retractor With Gel CAP, now USPN 7,883,461 issued Feb. 8, 2011.
U.S. Appl. No. 12/815,986, filed Jun. 15, 2010; Title: Hand Access Laparoscopic Device, now USPN 7,878,974 issued Feb. 1, 2011.
U.S. Appl. No. 10/695,295, filed Oct. 28, 2003; Title: Surgical Gel Seal.
U.S. Appl. No. 11/132,741, filed May 18, 2005, now U.S. Patent No. RE42,379, issued May 17, 2011; Title: Gas-Tight Seal Accomodating Surgical Instruments With a Wide Range of Diameters.
U.S. Appl. No. 11/245,709, filed Oct. 7, 2005, now U.S. Patent No. 7,951,076, issued May 31, 2011; Title: Surgical Access System.
U.S. Appl. No. 11/330,661, filed Jan. 12, 2006; Title: Sealed Surgical Access Device.
U.S. Appl. No. 11/564,409, filed Nov. 29, 2006, now U.S. Patent No. 8,187,177, issued May 29, 2012; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008, now U.S. Patent No. 8,109,873, issued Feb. 7, 2012; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009 now U.S. Patent No. 8,105,234, issued Jan. 31, 2012; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010, now U.S. Patent No. 8,070,676, issued Dec. 6, 2011; Title: Surgical Access Apparatus and Method.
U.S. Appl. No. 12/960,458, filed Dec. 3, 2010, now U.S. Patent No. 8,016,755, issued Sep. 13, 2011; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007, now abandoned; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004, now abandoned; Title: Surgical Sealing Device.
U.S. Appl. No. 11/246,909, filed Oct. 11, 2005, now U.S. Patent No. 7,998,068, issued Aug. 16, 2011; Title: Instrument Access Device.
U.S. Appl. No. 11/291,089, filed Dec. 1, 2005, now abandoned; Title: A Surgical Sealing Device.
U.S. Appl. No. 11/486,383, filed Jul. 14, 2006, now U.S. Patent No. 8,021,296, issued Sep. 20, 2011; Title: Wound Retractor.
U.S. Appl. No. 11/785,752, filed Apr. 19, 2007, now abandoned; Title: Instrument Access Device.
U.S. Appl. No. 12/244,024, filed Oct. 2, 2008, now abandoned; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004, now U.S. Patent No. 7,753,901, issued Jul. 13, 2010; Title: Laparoscopic Instrument and Cannula Assembly and Related Surgical Method.
U.S. Appl. No. 13/105,179, filed May 11, 2011; Title: Surgical Access System.
U.S. Appl. No. 13/231,348, filed Sep. 13, 2011; Title: Surgical Access Apparatus and Method.
U.S. Appl. No. 13/312,393, filed Dec. 6, 2011; Title: Surgical Access Apparatus and Method.
U.S. Appl. No. 13/345,279, filed Jan. 6, 2012; Title: Surgical Retractor With Gel Pad.
U.S. Appl. No. 13/347,897, filed Jan. 11, 2012.
U.S. Appl. No. 13/421,730, filed Mar. 15, 2012; Title: Surgical Access Apparatus and Method.
U.S. Appl. No. 13/463,161, filed May 3, 2012.

U.S. Appl. No. 11/904,263, filed Sep. 26, 2007; Title: Laparoscopic Instruments With Trocar Systems and Related Surgical Method.
U.S. Appl. No. 12/221,901, filed Aug. 7, 2008.
U.S. Appl. No. 12/221,912, filed Aug. 7, 2008; Title: Laparoscopic Instruments and Trocar Systems and Related Surgical Method.
U.S. Appl. No. 12/228,028, filed Aug. 8, 2008.
U.S. Appl. No. 12/550,595, filed Aug. 31, 2009; Title: Surgical Port Assembly.
U.S. Appl. No. 12/550,617, filed Aug. 31, 2009; Title: Laparoscopic Instrument and Related Surgical Method.
U.S. Appl. No. 12/636,038, filed Dec. 11, 2009; Title: Laparoscopic Instrument and Trocar Systems for Trans-Umbilical Laparoscopic Surgery.
U.S. Appl. No. 12/636,060, filed Dec. 11, 2009; Title: Laparoscopic Instrument and Trocar Systems for Transumbilical Laparoscopic Surgery.
U.S. Appl. No. 12/636,081, filed Dec. 11, 2009; Title: Laparoscopic Instrument and Trocar Systems for Trans-Umbilical Laparoscopic Surgery.
U.S. Appl. No. 12/636,104, filed Dec. 11, 2009; Title: Laparoscopic Instrument and Trocar Systems for Trans-Umbilical Laparoscopic Surgery.
U.S. Appl. No. 12/779,294, filed May 13, 2010; Title: Laparoscopic Instrument and Cannula Assembly and Related Surgical Method.
U.S. Appl. No. 13/175,822, filed Jul. 1, 2011; Title: Instrucment Access Device.
U.S. Appl. No. 13/210,307, filed Aug. 15, 2011; Title: Wound Retractor.
U.S. Appl. No. 13/400,143, filed Feb. 20, 2012.
U.S. Appl. No. 13/456,375, filed Apr. 26, 2012.
Dexterity Protractor Instruction Manual by Dexterity Surgical, Inc., dated 1999.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and The Written Opinion of the International Searching Authority for International Application No. PCT/US2006/040154, mailed Jan. 30, 2007.
European Patent Office, International Search Report and The Written Opinion of the International Searching Authority for International Application No. PCT/US2006/040073, mailed Jan. 26, 2007.
European Patent Office, International Search Report and The Written Opinion of the International Searching Authority for International Application No. PCT/US2006/039905, mailed Jan. 17, 2007.
European Patent Office, International Search Report and The Written Opinion of the International Searching Authority for International Application No. PCT/US2006/039883, mailed Jan. 31, 2007.
European Patent Office, International Search Report and The Written Opinion of the International Searching Authority for International Application No. PCT/US2006/039800, mailed Apr. 16, 2007.
European Patent Office, International Search Report and The Written Opinion of the International Searching Authority for International Application No. PCT/US2006/039799, mailed Mar. 27, 2007.
European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484, mailed on Nov. 12, 2004.
International Searching Authority/US, International Search Report and the Written Opinion of the International Searching Authority for International Application No. PCT/US01/29682, mailed on Jun. 14, 2002.
McSweeney, Cannulation of the Rumen in Cattle and Buffaloes, Australian Veterniary Journal, Aug. 1989, vol. 66, No. 8, pp. 266-268.
Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan, dated 1992.
The International Bureau of WIPO, International Preliminary Report on Patentability, dated Aug. 29, 2006, for International Application No. PCT/US2004/028250.
The International Bureau of WIPO, International Preliminary Report on Patentability, dated Apr. 16, 2008, for International Application No. PCT/US2006/039799.
The International Bureau of WIPO, International Preliminary Report on Patentability for International Application No. PCT/US2006/039800 dated Apr. 16, 2008.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, Laparascopic cholecystecomy via two ports, using the "Twin-Port" system, J. Hepatobiliary Pancreat Surg (2001) 8:76-80, dated Feb. 20, 2001.
International Search Report and Written Opinion in PCT/IE2005/000113 mailed on Feb. 22, 2006.
International Search Report and Written Opinion in PCT/IE2007/000050 mailed on Aug. 13, 2007.
Declaration of John R. Brustad dated Dec. 10, 2009, submitted in U.S. Appl. No. 11/548,955, including Appendices A-D regarding product sales brochures and production drawings from 2001 and 2005.
The International Searching Authority, The International Search Report and Written Opinion of the International Searching Authority for International Application No. PCT/US08/63445, mailed Sep. 29, 2008.
The International Searching Authority, The International Search Report and Written Opinion of the International Searching Authority for International Application No. PCT/US08/063463 mailed Sep. 10, 2008.

The International Bureau of WIPO, International Preliminary Report on Patentability for International Application No. PCT/US2008/063463, dated Nov. 17, 2009, entitled "Surgical Retractor".
International Searching Authority-US, International Search Report and Written Opinion of the International Searching Authority for International Application No. PCT/US04/25511, mailed Nov. 7, 2007.
International Searching Bureau of WIPO, International Report on Patentability, for International Application No. PCT/US04/25511, mailed Dec. 6, 2007.
The International Bureau of WIPO, International Preliminary Report on Patentability for International Application No. PCT/US2008/063445, issued Nov. 17, 2009, entitled "Surgical Retractor with Gel Pad".
U.S. Appl. No. 10/913,565, filed Aug. 5, 2004; Title: Surgical Device With Tack-Free Gel and Method of Manufacture.
European Patent Office, European Search Report for European Patent No. 11172709.5, dated Aug. 16, 2011.
European Patent Office, European Search Report for European Patent No. 11172706.1, dated Aug. 16, 2011.
European Patent Office, European Search Report for European Patent No. 12151288, dated Feb. 10, 2012.
Joint Claim Construction and Prehearing Statement in USDC Central District of California, Southern Division; Case No. SACV11-01406-JVS (Anx) filed May 21, 2012 in 44 pages.
Order re Markman Briefing and Hearing in USDC Central District of California, Southern Division; Case No. SACV11-01406-JVS (Anx) filed Jun. 21, 2012 in 1 page.
Response to the Court's Jun. 21, 2012 Order Re Markman Briefing and Hearing (Docket No. 41) in USDC Central District of California, Southern Division; Case No. SACV11-01406-JVS (Anx) filed Jun. 29, 2012 in 5 pages.
Applied Medical Resources Corporation's Opening Claim Construction Brief in USDC Central District of California, Southern Division; Case No. SACV11-01406-JVS (Anx) filed Jul. 9, 2012 in 30 pages
Declaration of Matthew S. Bellinger in Support of Applied Medical Resources Corporation's Opening Claim Constructions Brief, with Exhibits 1-10 (pp. 1-162) in USDC Central District of California, Southern Division; Case No. SACV11-01406-JVS (Anx) filed Jul. 9, 2012 in 162 pages.
Declaration of Matthew S. Bellinger in Support of Applied Medical Resources Corporation's Opening Claim Constructions Brief, with Exhibits 1-10 (pp. 163-324) in USDC Central District of California, Southern Division; Case No. SACV11-01406-JVS (Anx) filed Jul. 9, 2012 in 162 pages.
Declaration of John Brustad in Support of Applied Medical Resources Corporation's Opening Claim Construction Brief in USDC Central District of California, Southern Division; Case No. SACV11-01406-JVS (Anx) filed Jul. 9, 2012 in 6 pages.
Declaration of Dr. James C. Earthman in Support of Applied Medical Resources Corporation's Opening Claim Construction Brief, with Exhibit A in USDC Central District of California, Southern Division; Case No. SACV11-01406-JVS (Anx) filed Jul. 9, 2012 in 49 pages.
Declaration of Caryn Harsche Cross, with Exhibits A-G in USDC Central District of California, Southern Division; Case No. SACV11-01406-JVS (Anx) filed Jul. 9, 2012 in 140 pages.
Defendant Covidien's Opening Claim Construction Brief in USDC Central District of California, Southern Division; Case No. SACV11-01406-JVS (Anx) filed Jul. 9, 2012 in 30 pages.
Declaration of Caryn Harsche Cross, with Exhibits H-P In USDC Central District of California, Southern Division; Case No. SACV11-01406-JVS (Anx) filed Jul. 23, 2012 in 178 pages.
Defendant Covidien's Responsive Claim Constructions Brief in USDC Central District of California, Southern Division; Case No. SACV11-01406-JVS (Anx) filed Jul. 23, 2012 in 30 pages.
Applied Medical Resources Corporation's Responsive Claim Construction Brief in USDC Central District of California, Southern Division; Case No. SACV11-01406-JVS (Anx) filed Jul. 23, 2012 in 26 pages.
Second Declaration of Matthew S. Bellinger in Support of Applied Medical Resources Corporation's Responsive Claim Construction Brief, with Exhibits 11-12 in USDC Central District of California, Southern Division; Case No. SACV11-01406-JVS (Anx) filed Jul. 23, 2012 in 15 pages.
Order re Supplemental Briefing in USDC Central District of California, Southern Division; Case No. SACV11-01406-JVS (Anx) filed Jul. 25, 2012 in 1 page.
Applied Medical Resources Corporation's Supplemental Claim Construction Brief Pursuant to the Court's Jul. 25, 2012 Order (Dkt. No. 55) in USDC Central District of California, Southern Division; Case No. SACV11-01406-JVS (Anx) filed Jul. 31, 2012 in 7 pages.
Tentative Order re Claim Construction in USDC Central District of California, Southern Division; Case No. SACV11-01406-JVS (Anx) of Aug. 3, 2012 in 19 pages.
European Patent Office, Supplementary European Search Report for European Patent Application No. 08755322, dated Apr. 18, 2012.
European Patent Office, Supplementary European Search Report for European Patent Application No. 08755336, dated Jun. 15, 2012.
Civil Minutes re Claim Construction in USDC Central District of California, Southern Division; Case No. SACV11-01406-JVS (Anx) of Aug. 6, 2012 in 1 page.
Order re Claim Construction in USDC Central District of California, Southern Division; Case No. SACV11-01406-JVS (Anx) of Aug. 9, 2012 in 21 pages.
Complaint for Infringement of U.S. Patent No. 8,016,755 and Demand for Jury Trial in USDC Central District of California, Southern Division; Case No. SACV11-01406 JVC (ANx) filed Sep. 13, 2011 in 46 pages.
Amended Complaint for Infringement of U.S. Patent No. 8,016,755 and Demand for Jury Trial in USDC Central District of California, Southern Division; Case No. SACV11-01406 JVC (ANx) filed Oct. 4, 2011 in 46 pages.
Defendant Covidien's Answer, Defenses, Counterclaims, and Demand for Jury Trial in USDC Central District of California, Southern Division; Case No. SACV11-01406 JVC (ANx) filed Nov. 3, 2011 in 26 pages.
Applied Medical Resources Corporation's Answer to Counterclaims in USDC Central District of California, Southern Division; Case No. SACV11-01406 JVC (ANx) filed Dec. 1, 2011 in 8 pages.
Defendant Covidien's Disclosure of Invalidity Contentions with Exhibits A-E in USDC Central District of California, Southern Division; Case No. SACV11-01406 JVC (ANx) in 175 pages.
Defendant Covidien's Notice of Motion and Motion to Supplement Invalidity Contentions; Memorandum of Points and Authorities in Support Thereof in USDC Central District of California, Southern Division; Case No. SACV11-01406 JVC (ANx) filed Sep. 19, 2011 in 8 pages.
Minute Order re Motion to Supplement Invalidity Contentions in USDC Central District of California, Southern Division; Case No. SACV11-01406-JVS (ANx) of Oct. 18, 2012, in 2 pages.
Defendant Covidien's Disclosure of Supplemental Invalidity Contentions in USDC Central District of California, Southern Division; Case No. SACV11-01406 JVC (ANx) dated Oct. 19, 2012 in 56 pages.
Kagaya, Tadashi, Laparoscopic Cholecystectomy via two ports, using the "Twin-Port" system, J Hepatobiliary Pancreat Surg (2001) 8:76-80 in 5 pages.
Award of Arbitrators in International Centre for Dispute Resolution, International Arbitration Tribunal, In the Matter of the Arbitration between *Applied Medical Resources Corporation* vs. *Gaya Limited*, dated Feb. 29, 2008 in 10 pages.
Covidien Launches SILS™ Port Multiple Instrument Access Port, *Revolutionary New Laparoscopic Access Device Will Enable SILS™ Procedures*, dated Apr. 21, 2009, in 2 pages.
Rivas, Homero, MD, MBS, FACS, SILS™ Port Insertion brochure by Covidien, 2009 copyright date, in 4 pages.
Covidien SILS Port Instructions for Use, Flexible Port, 2011 copyright date, in 2 pages.
Rodgriguez, Ferdinand, *Principles of Polymer Systems*, 1970 copyright date, in 74 pages.
Gunnerson, Lee E., *Shell Kraton G Thermoplastic Rubber*, 1973 copyright date, in 4 pages.
*KRATON G 1652 Thermoplastic rubber*, Technical Bulletin Shell Chemical Company, presumably dated 1985, in 1 page.

*Solution Behavior of KRATON Thermoplastic rubbers*, Technical Bulletin Shell Chemical Company, presumably dated 1985, in 13 pages.
*KRATON Thermoplastic Rubber Medical Products*, Technical Bulletin Shell Chemical Company, presumably dated 1988, in 3 pages.
*Gas permeability of KRATON Rubbers*, Technical Bulletin Shell Chemical Company, dated May 1988, in 4 pages.
*KRATON Thermoplastic Rubber*, Typical Properties 1988, printed in May 1988, in 13 pages.
*KRATON Thermoplastic Rubber*, printed in Oct. 1989, in 43 pages.
*KRATON Thermoplastic Rubbers in oil gels*, Technical Bulletin Shell Chemical Company, dated Apr. 1989, in 11 pages.
*KRATON Polymers and Compounds*, Typical Properties Guide, 1998 copyright date, in 8 pages.
Defendant Covidien's Responses and Objections to Plaintiff Applied Medical Resources Corporation's First Set of Interrogatories (Nos. 1-11) Response Nos. 3, 10 Outside Counsel Eyes Only [Redacted] in USDC Central District of California, Southern Division; Case No. SACV11-01406 JVS (ANx) dated Jan. 23, 2012 in 22 pages.
Defendant Covidien's Second Supplement Responses and Objections to Plaintiff Applied Medical Resources Corporation's First Set of Interrogatories (No. 7) in USDC Central District of California, Southern Division; Case No. SACV11-01406 JVS (ANx) dated Apr. 23, 2012 in 11 pages.
Defendant Covidien's First Supplemental Initial Disclosures in USDC Central District of California, Southern Division; Case No. SACV11-01406 Jvs (ANx) dated Nov. 30, 2012 in 13 pages.
Defendant Covidien's [Proposed] Disclosure of Second Supplemental Invalidity Contentions, dated Nov. 30, 2012 in 11 pages.
Defendant Covidien's [Proposed] Amended Answer, Defenses, Counterclaims, and Demand for Jury Trial, of Nov. 30, 2012 in 50 pages.
Defendant Covidien's [Proposed] Amended Answer, Defenses, Counterclaims, and Demand for Jury Trial [Redline Document], of Nov. 30, 2012 in 52 pages.
Defendant Covidien's Memorandum of Points and Authorities in Support of Notice of Motion and Motion to Supplement Invalidity Contentions [Redacted] in USDC Central District of California, Southern Division; Case No. SACV11-01406 JVS (ANx) filed Dec. 18, 2012 in 10 pages.
Declaration of Slaven Jesic re Covidien's Notice of Motion and Motion to Supplement Invalidity Contentions [Redacted] with Exhibits A-F in USDC Central District of California, Southern Division; Case No. SACV11-01406 JVS (ANx) filed Dec. 18, 2012 in 23 pages.
Memorandum in Support of Defendant Covidien's Notice of Motion and Motion to Modify Scheduling Order and for Leave to File First Amended Answer, Affirmative Defenses, and Counterclaims [Redacted] in USDC Central District of California, Southern Division; Case No. SACV11-01406 JVS (ANx) filed Dec. 18, 2012 in 15 pages.
Declaration of Slaven Jesic re Covidien's Motion to Modify Scheduling Order and Motion for Leave to File First Amended Answer, Affirmative Defenses, and Counterclaims [Redacted] with Exhibits A-G in USDC Central District of California, Southern Division; Case No. SACV11-01406 JVS (ANx) filed Dec. 18, 2012 in 119 pages.
Declaration of Matthew S. Bellinger in Support of Applied's Oppositions to Defendant Tyco Healthcare Group LP's d/b/a Covidien Motion to Supplement Invalidity Contentions and Covidien's Motion to Modify Scheduling Order and for Leave to File First Amended Answer, Affirmative Defenses, and Counterclaims with Exhibits 1-8 in support thereof in USDC Central District of California, Southern Division; Case No. SACV11-01406 JVS (ANx) filed Dec. 24, 2012 in 204 pages.
Applied's Opposition to Covidien's Motion to Modify Scheduling Order and for Leave to File First Amended Answer, Affirmative Defenses, and Counterclaims [Redacted] in USDC Central District of California, Southern Division; Case No. SACV11-01406 JVS (ANx) filed Jan. 9, 2013 in 24 pages.
Applied's Opposition to Covidien's Motion to Supplement Invalidity Contentions [Redacted] in USDC Central District of California, Southern Division; Case No. SACV11-01406 JVS (ANx) filed Jan. 9, 2013 in 27 pages.
Defendant Covidien's Reply Brief in Support of Its Motion to Supplement Invalidity Contentions [Redacted] in USDC Central District of California, Southern Division; Case No. SACV11-01406 JVS (ANx) filed Jan. 11, 2013 in 12 pages.
Defendant Covidien's Reply in Support of Its Motion to Modify Scheduling Order and for Leave to File First Amended Answer, Affirmative Defenses, and Counterclaims [Redacted] in USDC Central District of California, Southern Division; Case No. SACV11-01406 JVS (ANx) filed Jan. 11, 2013 in 12 pages.
Declaration of Caryn Harsche Cross in support of Covidien's Motion to Modify Scheduling Order and for Leave to File First Amended Answer, Affirmative Defenses, and Counterclaims and Motion to Supplement Invalidity Contentions [Redacted] with Exhibits A—P In USDC Central District of California, Southern Division; Case No. SACV11-01406 JVS (ANx) filed Jan. 11, 2013 in 109 pages.
Order Granting Defendant Covidien's Motion to Modify Scheduling Order and for Leave to Amend and Motion to Supplement Invalidity Contentions in USDC Central District of California, Southern Division; Case No. SACV11-01406 JVS (ANx) dated Jan. 14, 2013 in 11 pages.
Applied's Notice of Motion and Motion for Partial Summary Judgment of No Inequitable Conduct in USDC Central District of California, Southern Division; Case No. SACV11-01406 JVS (ANx) filed Dec. 17, 2012 in 6 pages.
Memorandum of Points and Authorities in Support of Applied's Motion for Partial Summary Judgment of No Inequitable Conduct in USDC Central District of California, Southern Division; Case No. SACV11-01406 JVS (ANx) filed Dec. 17, 2012 in 9 pages.
Applied's Statement of Uncontroverted Facts and Conclusions of Law in Support of Its Motion for Partial Summary Judgment of No Inequitable Conduct in USDC Central District of California, Southern Division; Case No. SACV11-01406 JVS (ANx) filed Dec. 17, 2012 in 5 pages.
Declaration of Curtis R. Huffmire in Support of Applied Medical Resources Corporation's Motion for Partial Summary Judgment of No Inequitable Conduct with Exhibits 1-26 in support thereof in USDC Central District of California, Southern Division; Case No. SACV11-01406 JVS (ANx) filed Dec. 17, 2012 in 381 pages.
Applied's Re-Notice of Motion and Motion for Partial Summary Judgment of No Inequitable Conduct in USDC Central District of California, Southern Division; Case No. SACV11-01406 JVS (ANx) filed Dec. 21, 2012 in 4 pages.
Stipulation to Continue Hearing Date for Applied's Motion for Partial Summary Judgment of No Inequitable Conduct in USDC Central District of California, Southern Division; Case No. SACV11-01406 JVS (ANx) filed Dec. 21, 2012 in 8 pages.
Order Granting Stipulation to Continue Hearing Date for Applied's Motion for Partial Summary Judgment of No Inequitable Conduct in USDC Central District of California, Southern Division; Case No. SACV11-01406 JVS (ANx) signed Jan. 4, 2013 in 3 pages.
Defendant Covidien's Opposition to Applied's Motion for Partial Summary Judgment of No Inequitable Conduct [Redacted] in USDC Central District of California, Southern Division; Case No. SACV11-01406 JVS (ANx) filed Jan. 11, 2013 in 11 pages.
Defendant Covidien's Statement of Genuine Disputes in Opposition to Applied Medical Resources Corp.'s Motion for Partial Summary Judgment of No Inequitable Conduct [Redacted] in USDC Central District of California, Southern Division; Case No. SACV11-01406 Jvs (ANx) filed Jan. 11, 2013 in 9 pages.
Declaration of Caryn Harsche Cross in support of Defendant Covidien's Opposition to Applied's Motion for Partial Summary Judgment of No Inequitable Conduct [Redacted] with Exhibits A-D in USDC Central District of California, Southern Division; Case No. SACV11-01406 JVS (ANx) filed Jan. 11, 2013 in 25 pages.
Applied's Notice of Withdrawal for Partial Summary Judgment of No Inequitable Conduct in USDC Central District of California, Southern Division; Case No. SACV11-01406 JVS (ANx) filed Jan. 15, 2013 in 3 pages.
Order Granting Application Sealing Documents Re Defendant Covidien's First Amended Answer, Defenses, Counterclaims, and Demand for Jury Trial in USDC Central District of California, Southern Division; Case No. SACV11-01406 JVS (ANx) signed Jan. 30, 2013 in 2 pages.

Defendant Covidien's Amended Answer, Defenses, Counterclaims, and Demand for Jury Trial [Redacted] in USDC Central District of California, Southern Division; Case No. SACV11-01406 JVS (ANx) filed Feb. 6, 2013 in 50 pages.
Applied Medical Resources Corporation's Answer to Amended Counterclaims in USDC Central District of California, Southern Division; Case No. SACV11-01406 JVS (ANx) filed Feb. 11, 2013 in 15 pages.
Stipulation to Extend Dates and to Allow Covidien to File Amended Pleading in USDC Central District of California, Southern Division; Case No. SACV11-01406 JVS (ANx) consol/w SACV 13-24JVS (ANx) filed Feb. 15, 2013 in 13 pages.
Order on Stipulation to Extend Dates and Allow Covidien to File Amended Pleading in USDC Central District of California, Southern Division; Case No. SACV11-01406 JVC (ANx) consol/w SACV 13-24JVS (ANx) signed Feb. 19, 2013 in 4 pages.
Civil Cover Sheet in USDC Central District of California, Southern Division; Case No. SACV13-00024 JST (ANx) filed Jan. 4, 2013 in 3 pages.
Complaint Demand for Jury Trial in USDC Central District of California, Southern Division; Case No. SACV13-00024 JST (ANx) filed Jan. 4, 2013 in 12 pages.
Exhibit A to Complaint Demand for Jury Trial in USDC Central District of California, Southern Division; Case No. SACV13-00024 JST (ANx) filed Jan. 4, 2013 in 32 pages.
Exhibit B to Complaint Demand for Jury Trial in USDC Central District of California, Southern Division; Case No. SACV13-00024 JST (ANx) filed Jan. 4, 2013 in 32 pages.
Exhibit C to Complaint Demand for Jury Trial in USDC Central District of California, Southern Division; Case No. SACV13-00024 JST (ANx) filed Jan. 4, 2013 in 37 pages.
Exhibit D to Complaint Demand for Jury Trial in USDC Central District of California, Southern Division; Case No. SACV13-00024 JST (ANx) filed Jan. 4, 2013 in 38 pages.
Exhibit E to Complaint Demand for Jury Trial in USDC Central District of California, Southern Division; Case No. SACV13-00024 JST (ANx) filed Jan. 4, 2013 in 10 pages.
Exhibit F to Complaint Demand for Jury Trial in USDC Central District of California, Southern Division; Case No. SACV13-00024 JST (ANx) filed Jan. 4, 2013 in 11 pages.
Certification and Notice of Interested Parties (Local Rule 7.1-1) in USDC Central District of California, Southern Division; Case No. SACV13-00024 JST (ANx) filed Jan. 4, 2013 in 2 pages.
Notice of Related Cases Pursuant to L.R. 83-1.3 in USDC Central District of California, Southern Division; Case No. SACV13-00024 JST (ANx) filed Jan. 4, 2013 in 3 pages.
Report on the Filing or Determination of an Action Regarding a Patent or Trademark in USDC Central District of California, Southern Division; Case No. SACV13-00024 JST (ANx) filed Jan. 4, 2013 in 1 page.
Covidien's Initial Disclosures Related to SACV13-24 JVS (ANx) in USDC Central District of California, Southern Division; Case No. SACV Nov. 1406 JVS (ANx) Consolidated with SACV13-24 JVS (ANx) dated Feb. 22, 2013 in 14 pages.
Plaintiff Gaya Limited's Initial Disclosures in USDC Central District of California, Southern Division; Case No. 8:13 CV 00024-JVS-AN dated Feb. 20, 2013 in 6 pages.
Defendant Applied Medical Resources Corporation's Initial Disclosures in USDC Central District of California, Southern Division; Case No. SACV13-00024 JVS (ANx) dated Feb. 22, 2013 in 7 pages.
Defendant Covidien's Second Amended Answer, Defenses, Counterclaims, and Demand for Jury Trial [Redacted] in USDC Central District of California, Southern Division; Case No. SACV 11-01406 JVS(ANx) Consolidated with SACV13-24 JVS (ANx) dated Feb. 21, 2013 in 51 pages.
Applied Answer to Complaint in USDC Central District of California, Southern Division; Case No. SACV13-00024 JVS (ANx) dated Feb. 11, 2013 in 10 pages.
Rebuttal Expert Report of Dr. Alan Jeffrey Giacomin in USDC Central District of California, Southern Division; Case No. SACV11-01406 JVS (ANx) dated Feb. 8, 2013 in 142 pages.

Defendant Covidien's Disclosure of Second Supplemental Invalidity Contentions in USDC Central District of California, Southern Division; Case No. SACV11-01406 JVS (ANx) dated Jan. 29, 2013 in 11 pages.
Office Action in co-pending U.S. Appl. No. 13/231,348 dated Jan. 4, 2013 in 54 pages.
Applied Medical Resources Corporation's Answer to Covidien's Second Amended Answer, Defenses and Counterclaims in USDC Central District of California, Southern Division; Case No. SACV11-01406 JVS (ANx) filed Mar. 8, 2013 in 16 pages.
Office Action in co-pending U.S. Appl. No. 13/347,897 dated Mar. 11, 2013 in 10 pages.
Defendant Covidien's; Memorandum of Points and Authorities in Support of Notice of Motion and Motion to Supplement Invalidity Contentions [Subject to Protective Order] in USDC Central District of California, Southern Division; Case No. SACV11-01406 JVS (ANx) dated Dec. 10, 2012 in 10 pages.
Declaration of Slaven Jesic re Covidien's Notice of Motion and Motion to Supplement Invalidity Contentions with Exhibits A-F [Subject to Protective Order] in USDC Central District of California, Southern Division; Case No. SACV11-01406 Jvc (ANx) dated Dec. 10, 2012 in 29 pages.
Memorandum in Support of Defendant Covidien's Notice of Motion and Motion to Modify Scheduling Order and for Leave to File First Amended Answer, Affirmative Defenses, and Counterclaims [Subject to Protective Order] in USDC Central District of California, Southern Division; Case No. SACV11-01406 JVC (ANx) dated Dec. 10, 2012 in 15 pages.
Declaration of Slaven Jesic re Covidien's Motion to Modify Scheduling Order and Motion for Leave to File First Amended Answer, Affirmative Defenses, and Counterclaims with Exhibit A—G [Subject to Protective Order] in USDC Central District of California, Southern Division; Case No. SACV11-01406 Jvc (ANx) dated Dec. 10, 2012 in 315 pages.
Applied's Opposition to Covidien's Motion to Modify Scheduling Order and for Leave to File First Amended Answer, Affirmative Defenses, and Counterclaims [Subject to Protective Order] in USDC Central District of California, Southern Division; Case No. SACV11-01406 JVC (ANx) filed Dec. 26, 2012 in 23 pages.
Applied's Opposition to Covidien's Motion to Supplement Invalidity Contentions [Subject to Protective Order] in USDC Central District of California, Southern Division; Case No. SACV11-01406 JVC (ANx) filed Dec. 26, 2012 in 26 pages.
Exhibits 1-5 to the Declaration of Matthew S. Bellinger in support of Applied's Opposition to Covidien's Motion to Modify Scheduling Order and for Leave to File First Amended Answer, Affirmative Defenses, and Counterclaims [Subject to Protective Order] in USDC Central District of California, Southern Division; Case No. SACV11-01406 JVC (ANx) filed Dec. 26, 2012, Exhibit 1: Award of Arbitrators in Applied v. Gaya Arbitration, Exhibit 2: Gaya's Arbitration Pre-hearing Memorandum, Exhibit 3: Applied's Arbitration Pre-hearing Brief, Exhibit 4: Gaya's Arbitration Post-hearing Memorandum, Exhibit 5: Applied's Post-hearing Brief, in 240 pages.
Defendant Covidien's Reply in Support of Its Motion to Modify Scheduling Order and for Leave to File First Amended Answer, Affirmative Defenses, and Counterclaims [Subject to Protective Order] in USDC Central District of California, Southern Division; Case No. SACV11-01406 JVC (ANx) dated Dec. 31, 2012 in 12 pages.
Defendant Covidien's Reply Brief in Support of Its Motion to Supplement Invalidity Contentions [Subject to Protective Order] in USDC Central District of California, Southern Division; Case No. SACV11-01406 JVC (ANx) dated Dec. 31, 2012 in 12 pages.
Declaration of Caryn Harsche Cross in support of Covidien's Motion to Modify Scheduling Order and Motion for Leave to File First Amended Answer, Affirmative Defenses, and Counterclaims and Motion to Supplement Invalidity Contentions with Exhibits A—P [Subject to Protective Order] in USDC Central District of California, Southern Division; Case No. SACV11-01406 JVC (ANx) dated Dec. 31, 2012 in 309 pages.
Defendant Covidien's Opposition to Applied's Motion for Partial Summary Judgment of No Inequitable Conduct [Subject to Protective Order] in USDC Central District of California, Southern Division; Case No. SACV11-01406 JVC (ANx) dated Jan. 7, 2013 in 11 pages.
Defendant Covidien's Statement of Genuine Disputes in Opposition to Applied Medical Resources Corp.'s Motion for Partial Summary Judgment of No Inequitable Conduct [Subject to Protective Order] in USDC Central District of California, Southern Division; Case No. SACV11-01406 JVC (ANx) dated Jan. 7, 2013 in 9 pages.
Declaration of Caryn Harsche Cross in support of Defendant Covidien's Opposition to Applied's Motion for Partial Summary Judgment of No Inequitable Conduct with Exhibits A-D [Subject to Protective Order] in USDC Central District of California, Southern Division; Case No. SACV11-01406 JVC (ANx) dated Jan. 7, 2013 in 21 pages.
Defendant Covidien's Third Supplemental Responses and Objections to Plaintiff Applied Medical Resources Corporation's First Set of Interrogatories (Nos. 4-6) [Subject to Protective Order] in USDC Central District of California, Southern Division; Case No. SACV11-01406 JVC (ANx) dated Nov. 30, 2012 in 33 pages.
Opening Expert Report of Prof. David F. Williams with Exhibits A-C [Subject to Protective Order] in USDC Central District of California, Southern Division; Case No. SACV11-01406 JVC (ANx) dated Dec. 6, 2012 in 100 pages.
Opening Expert Report of John M. Collins, Ph.D with Exhibits A-K [Subject to Protective Order] in USDC Central District of California, Southern Division; Case No. SACV11-01406 JVC (ANx) dated Dec. 6, 2012 in 343 pages.
*Applied Medical Resources Corporation* v. *Gaya Limited*, Case No. 50 133100316 06 Arbitration Hearing Transcript—vol. 1, dated Oct. 8, 2007 in 90 pages [Subject to Protective Order].
*Applied Medical Resources Corporation* v. *Gaya Limited*, Case No. 50 133100316 06 Arbitration Hearing Transcript—vol. 2, dated Oct. 9, 2007 in 85 pages [Subject to Protective Order].
*Applied Medical Resources Corporation* v. *Gaya Limited*, Case No. 50133T00316 06 Arbitration Hearing Transcript—vol. 3, dated Oct. 10, 2007 in 96 pages [Subject to Protective Order].
*Applied Medical Resources Corporation* v. *Gaya Limited*, Case No. 50133T00316 06 Arbitration Hearing Transcript—vol. 4, dated Oct. 11, 2007 in 103 pages [Subject to Protective Order].
Arbitration Exhibit 33—Medtech R & D Lab Book LN-001 issued to Damien Rosney, date range from Oct. 19, 1998 to Jan. 21, 2000, with handwritten notes, in 104 pages, [Subject to Protective Order].
Arbitration Exhibit 34—Cummins, Christy handwritten notes faxed to Martin Caldwell, dated Nov. 18, 1998 in 1 page, [Subject to Protective Order].
Arbitration Exhibit 39—Medtech R & D Lab Book LN-002 issued to Damien Rosney, date range from Feb. 9, 1999 to Mar. 6, 2001, with handwritten notes, in 69 pages, [Subject to Protective Order].
Arbitration Exhibit 43—Folder labeled Ideas Generations Wound Retractors with notes concerning design proposals regarding wound retractors, dated Apr. to Jul. 1999, in 29 pages, [Subject to Protective Order].
Arbitration Exhibit 50—Handwritten notes out of a 1999 calendar of Medtech consultant Christy Cummins, date range from Jul.-Aug. 1999, in 4 pages, [Subject to Protective Order].
Arbitration Exhibit 184—Bermingham, Donal (Medtech Ltd.), *Intromit Design Improvement Proposals*, dated Aug. 23, 2000 in 13 pages. [Subject to Protective Order].
Arbitration Exhibit 234—Letter from Christy Cummins to Martin Caldwell in 2 pages, dated Dec. 22, 2000 [Subject to Protective Order].
Arbitration Exhibit 466—Lab Notebook of Christy Cummins, handwritten pictures and notes, in 17 pages, date range from Sep.-Oct. 1998, [Subject to Protective Order].
Defendant Covidien's Amended Answer, Defenses, Counterclaims, and Demand for Jury Trial [Subject to Protective Order] in USDC Central District of California, Southern Division; Case No. 11-CV-1406 JVS (ANx) dated Jan. 29, 2013 in 50 pages.
Defendant Covidien's Second Amended Answer, Defenses, Counterclaims, and Demand for Jury Trial [Subject to Protective Order] in USDC Central District of California, Southern Division; Case No. 11-CV01406 JVS(ANx) Consolidated with SACV13-24 JVS (ANx) dated Feb. 21, 2013 in 51 pages.
Rebuttal Expert Report of James Craig Milroy Regarding Validity of U.S. Patent No. 8,016,755 [Subject to Protective Order] in USDC Central District of California, Southern. Division; Case No. SACV11-01406 JVS (ANx) dated Feb. 8, 2013 in 148 pages.
Covidien's Responses and Objections to Applied's Third Set of Interrogatories (Nos. 26-28) in USDC Central District of California, Southern Division; Case No. SACV11-01406 JVS (ANx) Consolidated with SACV13-24 JVS (ANx) dated Apr. 15, 2013, 2013 in 7 pages.
Covidien LP and Covidien Sales LLC Responses and Objections to First Set of Interrogatories (Nos. 19) in USDC Central District of California, Southern Division; Case No. SACV11-01406 JVS (ANx) Consolidated with SACV13-24 JVS (ANx) dated Apr. 15, 2013, 2013 in 19 pages.
Gaya's Responses and Objections to First Set of Interrogatories (Nos. 1-12) in USDC Central District of California, Southern Division; Case No. SACV11-01406 JVS (ANx) Consolidated with SACV13-24 JVS (ANx) dated Apr. 15, 2013, 2013 in 18 pages.
Applied's Responses to Covidien LP and Covidien Sales LLC's First Set of Interrogatories (Nos. 1-6) in USDC Central District of California, Southern Division; Case No. SACV11-01406 JVS (ANx) Consolidated with SACV13-24 JVS (ANx) dated Apr. 15, 2013, 2013 in 15 pages.

* cited by examiner

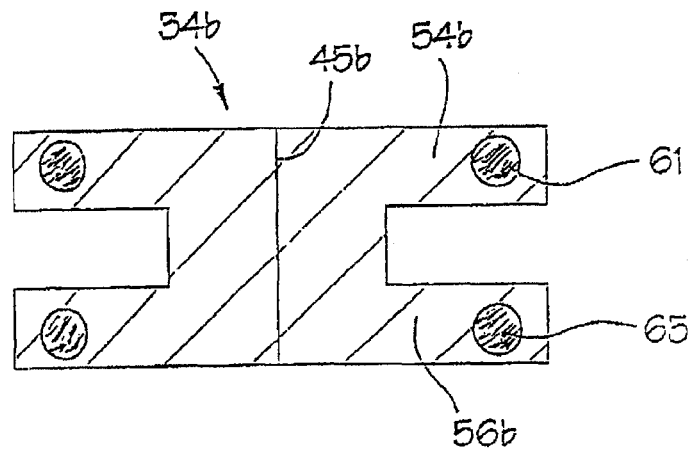
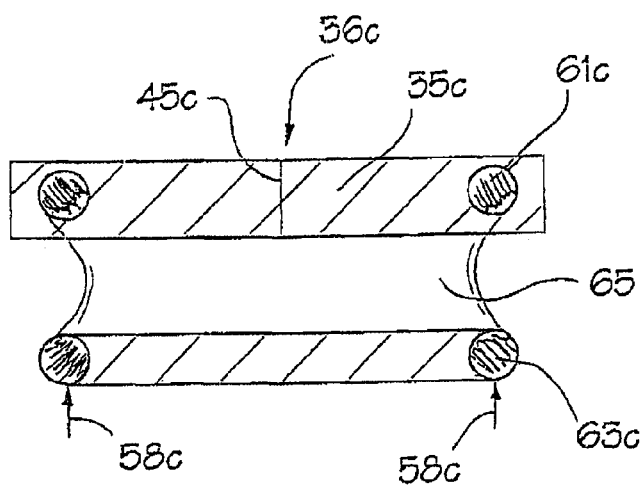
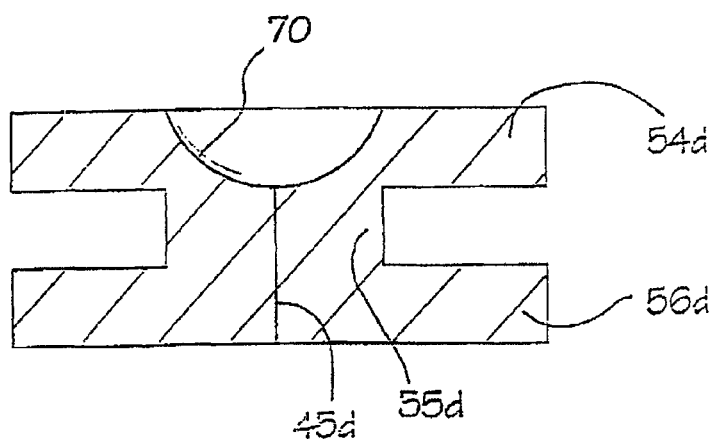

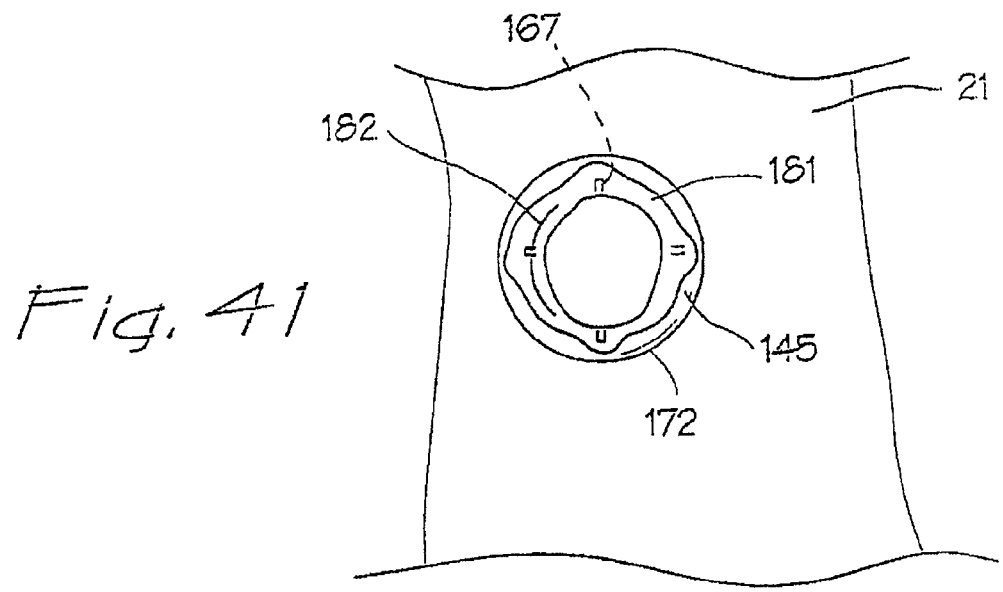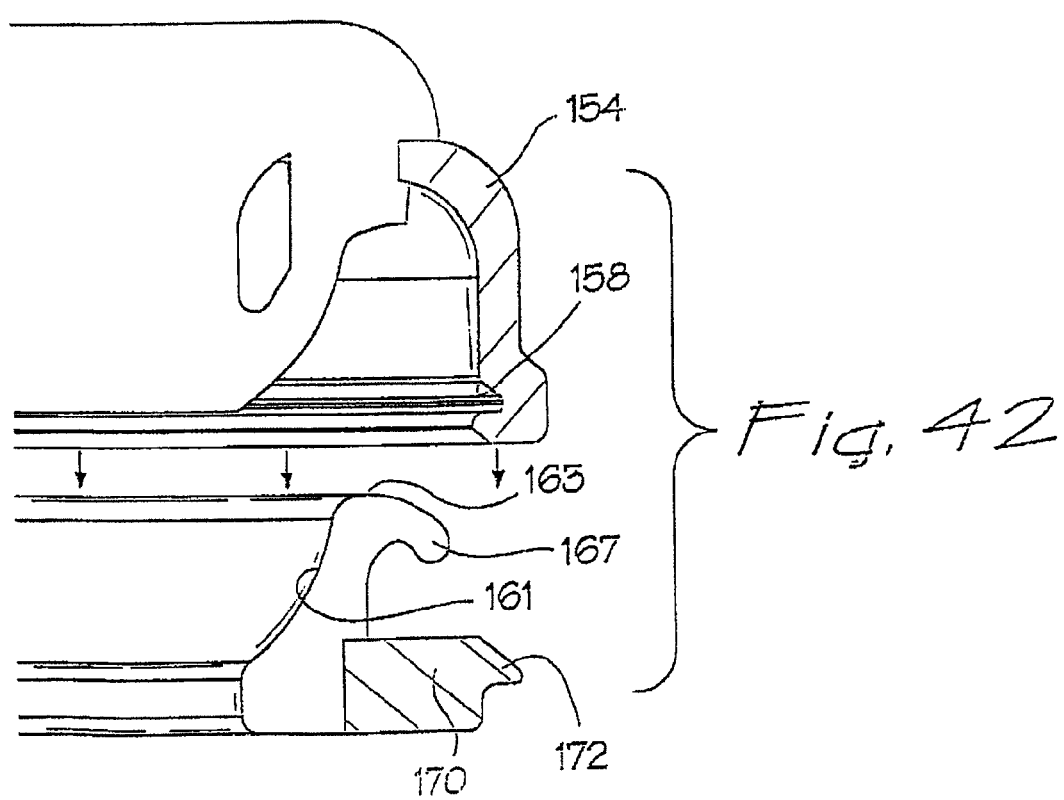

SURGICAL ACCESS APPARATUS AND METHOD

CROSS-REFERENCE TO RELATED APPLICATION

This application is a continuation of U.S. application Ser. No. 13/231,348, filed Sep. 13, 2011, pending, which is a continuation of U.S. application Ser. No. 12/960,458, filed Dec. 3, 2010, now U.S. Pat. No. 8,016,755, which is a continuation of U.S. application Ser. No. 12/360,710, filed Jan. 27, 2009, now U.S. Pat. No. 8,105,234, which is a continuation of U.S. application Ser. No. 11/244,647, filed Oct. 5, 2005, now U.S. Pat. No. 7,481,765, which is a continuation of U.S. application Ser. No. 10/381,220, filed Mar. 20, 2003, now U.S. Pat. No. 7,473,221, which is the National Phase application under 35 U.S.C. §371 of International Application No. PCT/US2001/029682, filed Sep. 21, 2001, which published in English as International Publication No. WO 2002/034108 A1 on May 2, 2002, which claims the benefit of U.S. application No. 60/241,958, filed Oct. 19, 2000, all of the disclosures of which are incorporated by reference.

BACKGROUND OF THE INVENTION

1. Field of the Invention

This invention relates generally to devices and other apparatus facilitating sealed access with surgical instruments, such as a surgeon's hand, across a body wall and into a body cavity.

2. Background of the Invention

In several areas of surgery there exists a need to have mechanisms or devices that can seal a body cavity or space, and yet permit the introduction of surgical instruments such as guidewires, endoscopes, and even the hand of a surgeon. Typical of these areas of surgery is laparoscopic surgery which relies on surgical instruments inserted through the abdominal wall to reach an operative site within the abdominal cavity. In order to increase space around the operative site within the cavity, insufflation gases are typically introduced to inflate the cavity and elevate the abdominal wall. This pressurizing of the abdominal cavity is referred to as pneumoperitoneum. In this context, the need to seal the body cavity or space arises from the need to maintain the pneumoperitoneum even when instruments are present.

Trocars have been commonly used to provide instrument access in laparoscopic surgeries. These trocars have included elaborate seal structures having zero seals which prevent escape of the gases in the absence of instruments, and instrument seals which prevent escape of the gases in the presence of instruments. Unfortunately, the instrument seals have been able to accommodate only a narrow range of instrument diameters. Where wider ranges were desired multiple seal pairs had to be provided.

Some instruments, such as the hand of the surgeon, have been too large for trocar access. Under these circumstances, hand-assisted laparoscopic seals have been provided. Such devices have been large, cumbersome, and largely ineffective in providing the required sealing mechanism. Other access devices, such as Touhy-Borst seals, have been used but only for very small diameter access such as that required by a guidewire.

Each of the prior devices suffers from drawbacks which make the device difficult or cumbersome to use. For example, a Touhy-Borst seal requires two hands to use and does not form a seal when a guidewire or other device is about to be introduced. Present trocar seals and hand-assisted seals require two valves, one forming an instrument seal in the presence of the instrument, and the other forming a zero seal in the absence of the instrument. For example, in hand-assisted devices, elaborate mechanisms have been required to seal around the surgeon's arm. When the arm is removed, a separate zero seal has been required to prevent the escape of blood or insufflation gases.

SUMMARY OF THE INVENTION

These deficiencies of the prior art are overcome with the present invention which includes both a seal apparatus and a method for using this apparatus to perform elaborate surgeries. In one embodiment, the device includes a valve structure formed of a gel including, for example, a thermoplastic base such as KRATON (a trademark of Shell Corporation) and an oil. The resulting elastomer has an excellent tear strength, elongation greater than 1,000 percent, a very low durometer or hardness, and biocompatibility. A process for manufacturing this device is greatly simplified using molding techniques.

Importantly, the access device can function as both a zero seal and an instrument seal. Furthermore, it can accommodate a full range of instrument diameters, such as a range from two French in the case of a guidewire, to three or four inches in the case of a surgeon's hand. In addition, several instruments can be accommodated at the same time with a single access device.

Both tear resistance and sealing capability can be enhanced by encapsulating the gel in a sheath or otherwise providing circumferential reinforcement for the valve structure. Additives can be provided either on or in the gel to enhance properties such as lubricity, appearance, wound treatment and/or protection, anti-cancer protection and anti-microbial protection. Additional chemicals, compounds, pharmaceuticals or even mechanical devices can be mixed with or embedded in the gel material to vary chemical, pharmaceutical or physical properties of the access device.

These and other features and advantageous of the invention will be clarified with a description of preferred embodiments and reference to the associated drawings.

DESCRIPTION OF THE DRAWINGS

FIG. 9 is a cross section view similar to FIG. 8 and illustrating an embodiment with circumferential reinforcement members;

FIG. 10 is an axial cross section view similar to FIG. 9 and illustrating a double-ring retractor with an access device of the present invention;

FIG. 11 is a radial cross section view similar to FIG. 8 and illustrating an embodiment having a lead-in cavity or pocket;

FIGS. 39-42 illustrate progressive steps in a preferred method of use associated with the embodiment of FIG. 32;

FIG. 39 is a top plan view showing use of a template;

FIG. 40 is a top plan view of showing placement of the retraction sheath;

FIG. 41 is a top plan view showing placement of the base ring and securement of the traction sheath; and FIG. 42 is an axial cross section view partially in section showing placement of the gel cap relative to the base.

DESCRIPTION OF PREFERRED EMBODIMENTS

Figure 1:
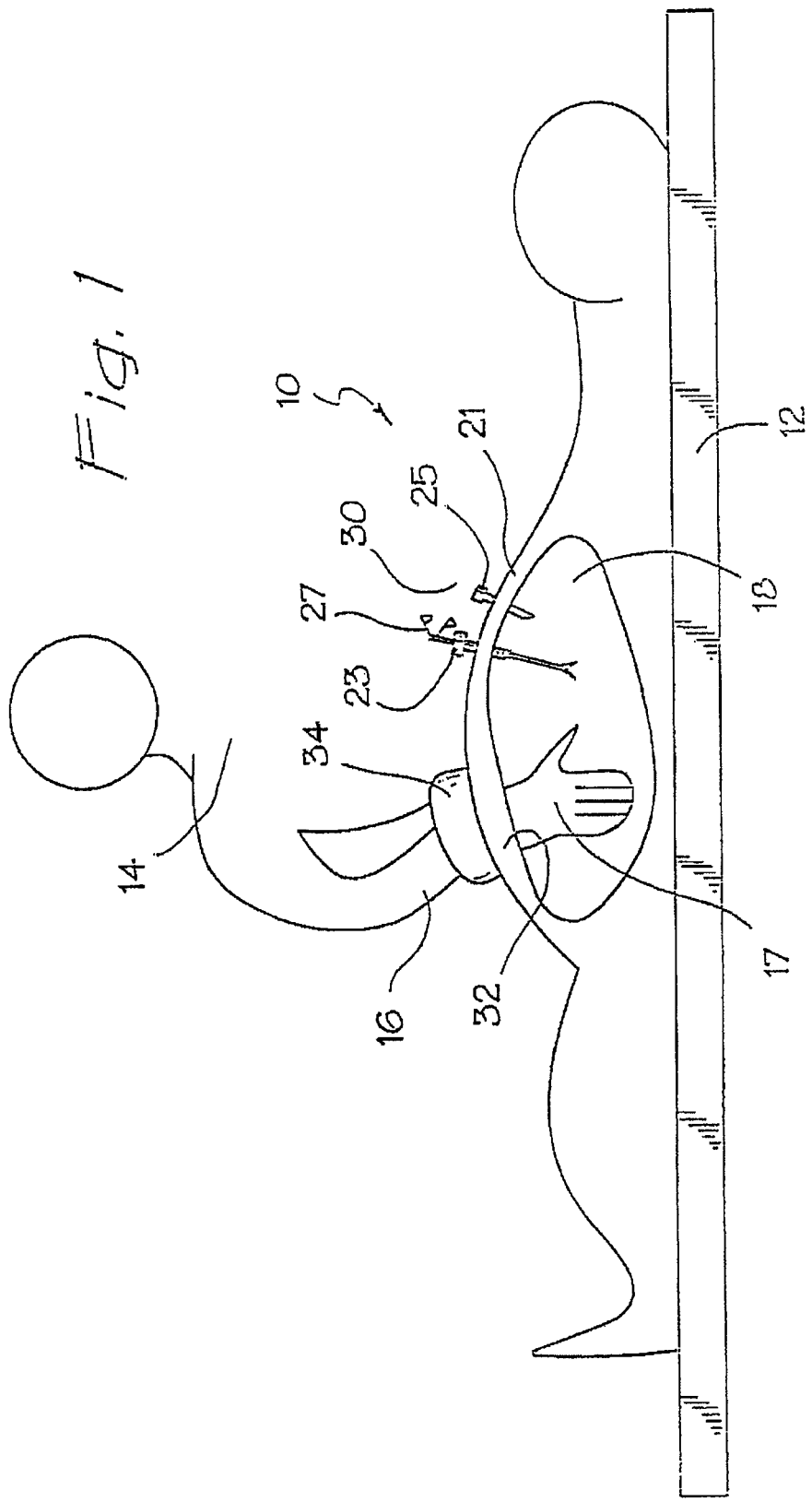
FIG. 1 is a perspective view showing a patient prone on an operating table with his abdomen insufflated, and with instrument access provided by trocars and the access device of the present invention.

A patient is illustrated in FIG. 1 and designated generally by the reference numeral 10. The patient 10 is shown in a prone position on an operating table 12, where abdominal surgery is being performed by a surgeon 14 having an arm 16 and a hand 17. In the illustrated example, the operative procedure is performed within an abdominal cavity 18 with instrument access provided through an abdominal wall 21. In this type of operation, commonly referred to as laparoscopic surgery, trocars 23 and 25 are commonly used to provide minimally invasive access through the abdominal wall 21 for instruments such as a grasper 27 and an endoscope 30

Although the specific focus of this disclosure will be on a preferred laparoscopic procedure, it will be noted that laparoscopic surgery is merely representative of a type of operation wherein a procedure can be performed in a body cavity with minimal access through a body wall.

Notwithstanding the foregoing generality, it is important to note that with respect to laparoscopic surgery, it is often desirable that the surgeon 14 be able to insert his/her hand 17 through the abdominal wall 21 and into the abdominal cavity 18. This insertion of the hand 17 provides the surgeon 14 with direct access to various elements of the anatomy In order to accommodate the hand 17 and arm 16 of the surgeon 14, a small incision 32 is typically created in the abdominal wall 21. An access device 34 of the present invention can be provided to further facilitate this access by the hand of the surgeon 14.

Particularly in the case of laparoscopic surgery, it is advantageous to insufflate the abdominal cavity 18 with a gas, such as carbon dioxide, in order to elevate the abdominal wall 21 and thereby increase the volume of the working space within the cavity 18. Maintenance of this insufflation pressure, commonly referred to as pneumoperitoneum, is particularly difficult where access is desired across the abdominal wall 21, for example, through the trocars 23, 25, as well as the access device 34. For this reason, a substantial effort has been directed to providing such access devices with sealing characteristics both in the presence of instruments and in the absence of instruments, such as the grasper 29, scope 30 and hand 27.

Thus, the trocars 23 and 25 have typically been provided with complex valve structures, including, for each narrow range of instrument sizes, an instrument valve which forms an instrument seal in the presence of an instrument, and a zero valve which forms a zero seal in the absence of an instrument. By providing both an instrument seal and a zero seal the valve structures have been able to inhibit the escape of gases through the trocars both in the presence and the absence of an instrument, respectively.

The instrument seals have been particularly cumbersome, as noted, and have only been effective for a small range of instrument diameters. For example, separate instrument seals have been needed for instruments, such as guidewires, which may have a diameter of only two French to three French. For medium-sized instruments having diameters of three millimeter to five millimeters, a second instrument seal has been required. In some cases, even a third instrument seal has been necessary in order to accommodate instruments having diameters such as nine millimeters to 12 millimeters.

Typically the varying sizes of instruments have also required individual zero seals for each range. Thus, in a complex trocar, such as the trocar 23, there might be as many as six separate seals associated with the access device.

If not for the desire to maintain the pneumoperitoneum, there would be no need for the trocars 23, 25 or the access device 34. One would merely cut an incision in the abdominal wall 21 and insert the instrument directly through the incision. However, without appropriate valves or seals, the insufflation gases would merely escape through the incisions. This would be particularly detrimental in the case of the incision 32 which must be sufficiently large to accept the hand 17 of the surgeon 14. Thus it is a primary purpose of the access device 34 to form with the incision 32 an access or working channel 34, and to provide a valve or other sealing structure across the working channel 34 in order to maintain the pneumoperitoneum.

Figure 2:
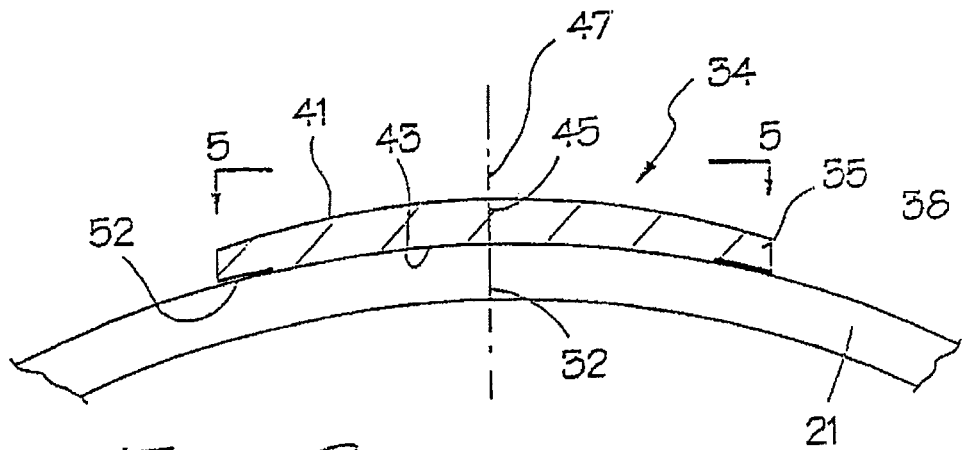
FIG. 2 is an enlarged side elevation view of the access device of FIG. 1 operatively disposed exteriorly as the abdominal wall.

An enlarged view of one embodiment of the access device 34 is illustrated in FIG. 2 which also shows the abdominal wall 21 and the incision 32. In this simple form, the access device 34 has the general configuration of a pad 35, meaning that it is generally flat and disposed in a plane such as the plane 38. Typically parallel to this plane 38 are a pair of major surfaces of 41 and 43 which provide the pad 35 with a substantial surface area. An opening or slit 45 can be formed through the pad 35, generally along an axis 47 perpendicular to the plane 38.

Figure 3:
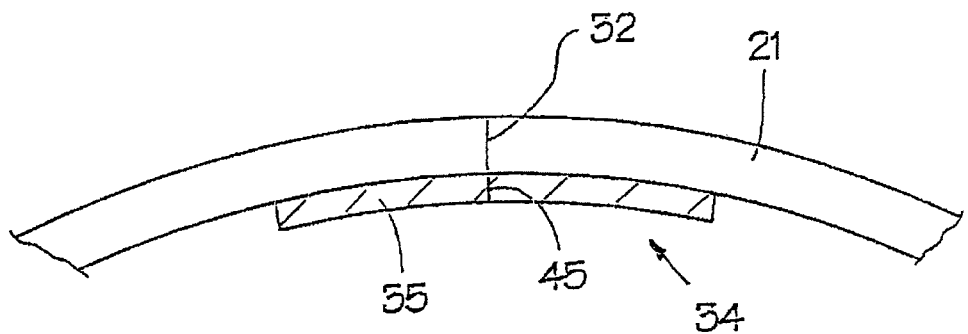
FIG. 3 is a side elevation view similar to FIG. 2 showing the access device operatively disposed interiorly of the abdominal wall.
Figure 4:
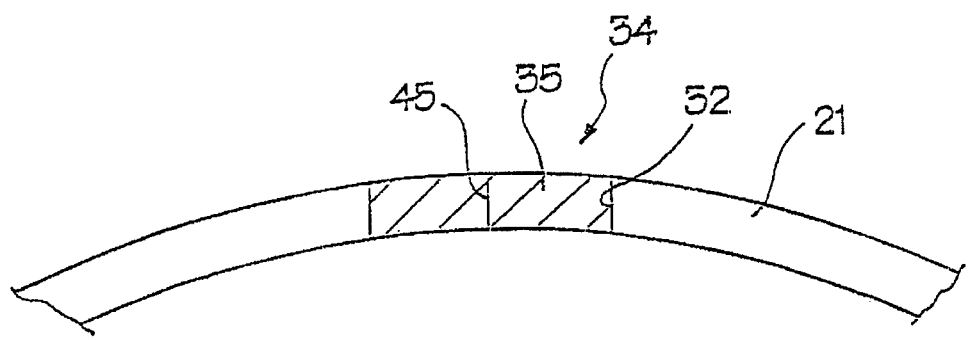
FIG. 4 is a side elevation view similar to FIG. 2 showing the access device operatively disposed within an incision in the abdominal wall.

When operatively disposed, the opening 45 of the pad 35 is in communication with the incision 32 and, in this case, forms with the incision 32, the working channel 36. The alignment of the opening 45 and incision 32 can occur with the pad 35 disposed exteriorly of the abdominal wall as illustrated in FIG. 2, interiorly of the abdominal wall is 21 as illustrated in FIG. 3, or within the abdominal wall 21 as illustrated in FIG. 4. In any of these positions, operative disposition of the pad 35 relative to the abdominal wall 21 requires that the pad 35 be maintained in its operative position and that it form a seal around the incision 32. Referring to the plan view of FIG. 5, these two functions are accomplished with an adhesive 50 disposed around the incision 32 between the pad 35 and the abdominal wall 21.

Figure 5:
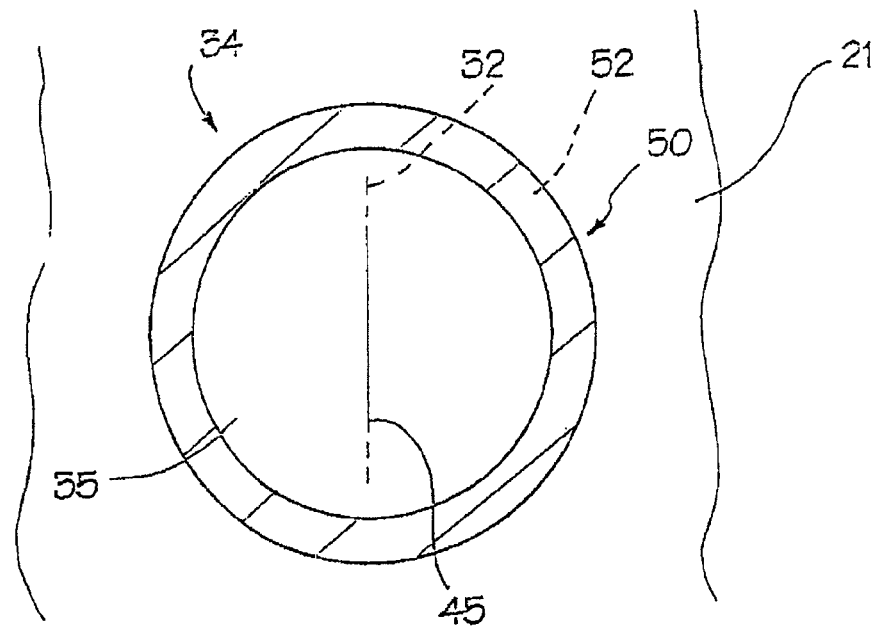
FIG. 5 is a plan view taken along lines 5-5 of FIG. 2.

If this adhesive 50 is formed as a continuous ring 52, as illustrated in FIG. 5, the pad 35 can be disposed with the ring 52 positioned circumferentially around the incision 32 to form a seal between the pad 35 and the abdominal wall 21. In the illustrated example, when the pad 35 is operatively positioned, the escape of insufflation gases is inhibited between the pad 35 and the abdominal wall 21 by the adhesive ring 52.

The escape of insufflation gases is inhibited through the opening 45 of the pad 35 by the self-sealing characteristics of the material forming the pad 35. This material and its highly advantageous properties are discussed in significant detail below.

It will be appreciated that the functions of the adhesive ring 52 can be accomplished in many different ways using many different materials and shapes. For example, many materials other than adhesives can be used to maintain the pad 35 in position over the incision 32. The formation of a seal around the incision 32 can also be accomplished with methods other than adhesion. Furthermore, the shape of the continuous seal formed by the adhesive 50 need not be in the shape of a circle. Rather, any continuous pattern sufficiently large to form a perimeter around the incision 32 could facilitate the desired sealing relationship. Finally, it will be noted that the mere placement of the pad 35, for example, interiorly of the abdominal wall 21 as illustrated in FIG. 3, may produce a perimeter seal merely as a result of the insufflation pressure.

Figure 6:
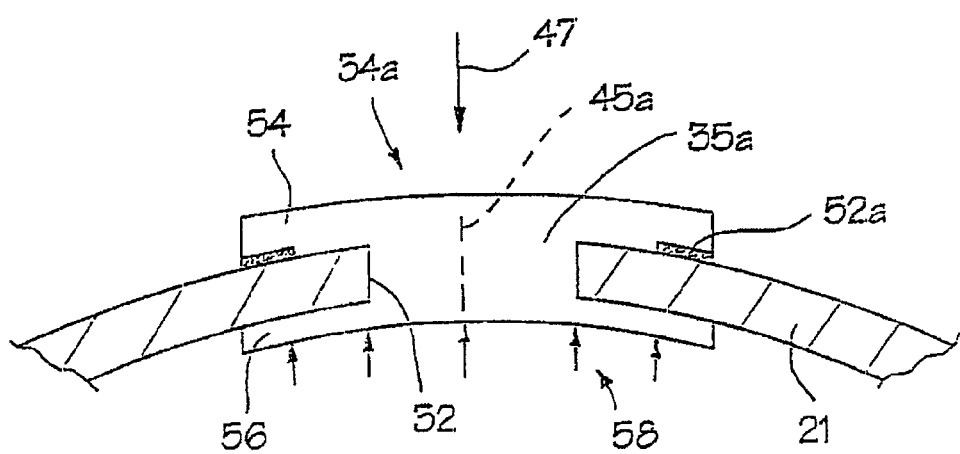
FIG. 6 is a side elevation view similar to FIG. 2 and illustrating a further embodiment of the access device having an external flange and an internal flange.

A further embodiment of the access device 34 is illustrated in FIG. 6 where elements of structure similar to those previously disclosed or designated with the same reference numeral followed by the lower case "a." In this embodiment, the functions of position-maintenance and sealing are accomplished with an alternative configuration for the access device itself. The pad 35 in this case is disposed within the incision 32 as illustrated in FIG. 4. However, an external flange 54 and an internal flange 56 are formed integral with the pad 35. As shown, for example, in the axial cross section view of FIG. 8, the access pad with flanges is formed monolithically.

When operatively disposed, the external flange 54 is positioned outside of the abdominal wall 21 while the internal flange 56 is disposed interiorly of the abdominal wall 21a. In this matter, the pad 35 can be disposed within the incision 32a and held in position by the flanges 54, 56. When the hand 17 of the surgeon 14 is inserted through the access device 34, the exterior flange 54 prevents the pad 35a from moving distally. Similarly, when the hand 17 of the surgeon 14 is withdrawn, the interior flange 56 prevents the pad 35a from moving proximally In this embodiment, the opening 45a extends through the pad 35a as well as the flanges 54 and 56, and completely defines the working channel 34 through the incision 32.

The primary seal which is required between the access device 34a and the abdominal wall 21, can be formed with the adhesive ring 52a as discussed with reference to FIG. 6. Alternatively, this embodiment including the interior flange 56 may rely merely upon the surface contact between the flange 56a and the abdominal wall 21. In this case, the primary seal can be formed between these structural elements and enhanced by the pneumoperitoneum pressure which forces the interior flange 56 against the abdominal wall as illustrated by a plurality of arrows 58. This seal is formed primarily in a radial plan generally perpendicular to the axis 47.

The function of the primary seal may be further enhanced by additional sealing which occurs between the pad 35a and the portions of the abdominal wall 21 forming the incision 32. In this location, the abdominal wall 21 is radially compressed by the mere presence of the pad 35 within the incision 32. The resulting pressure produces an axial seal between the pad 35a and the abdominal wall 21.

If the adhesive ring 52a is desired for this embodiment, it is most advantageously placed around the incision 32, between the exterior flange 54 and the abdominal wall 21.

It will be noted that whenever an instrument, such as the arm 16 or hand 17 of the surgeon 14, is inserted through the pad 35, the material of the pad conforms to the surface of the instrument and forms the instrument seal with the instrument. Accordingly, during the entire period beginning with insertion of the instrument and ending with withdrawal of the instrument, there is substantially no loss of insufflation gas through the pad 35a nor any loss of pneumoperitoneum within the abdominal cavity 18.

Figure 7:
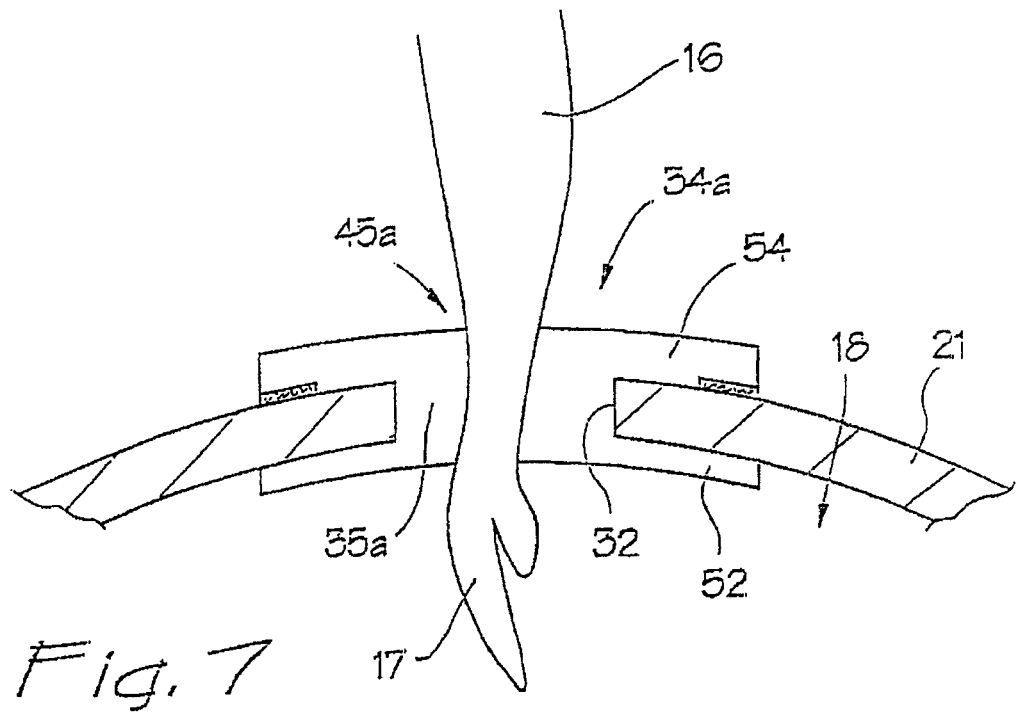
FIG. 7 is a side elevation view similar to FIG. 6 and illustrating the hand of a surgeon being inserted through the access device.

With further reference to FIG. 7, it will be appreciated that the arm 16 and hand 17 of the surgeon 14 are merely examples of instruments which can be inserted through the access device 34a. In the absence of the instrument, or hand 17 in the case of FIG. 7, the opening or slit 45a merely closes against itself to form a zero seal, thus preventing the escape of insufflation gases through the access device 34a. When the instrument, such as the hand 17, is inserted through the opening or slit 45a, an instrument seal is formed between the material of the access device 34a and the exterior surface of the instrument. This prevents the escape of insufflation gases through the access device 34a, even when an instrument is present. Thus, insufflation pressures can be maintained within the abdominal cavity 18 whether or not the instrument is in place. Note that these seals, the zero seal and the abdominal seal, can be formed as a single valve structure having properties for accommodating a full range of instrument sizes.

Formation of the pad 35a will typically be accomplished in a simple molding process described in greater detail below. In such a process, the opening or slit 45a may be formed as part of the molding process.

In most cases, the single access opening 45a will be sufficient to accommodate the operative procedure. However, a further advantage of the access device 34a will be particularly appreciated by the surgeon 14 who requires even more access through the pad 35a. Consider for example, the surgeon 14 having his/her arm 16 inserted through the opening 45a when he/she decides that a further instrument is required for the operative procedure. Under these circumstances, a further opening through the pad 35a can be established by merely inserting the desired operative instrument through the pad 35a. In this manner, the instrument can create its own access hole beside the primary opening 45a.

Particularly for those operative instruments having pointed distal ends, the instrument can merely be forced through the pad 35a forming its own access hole, such as the opening 45a, as it is moved distally. This opening, created by the operative instrument itself, would automatically form an instrument seal as the instrument is inserted, as well as a zero seal as the instrument is withdrawn.

For operative instruments not having pointed distal ends, it is possible to form a new access hole using a secondary instrument, such as a trocar obturator. After the access hole is formed, the obturator can be removed, vacating the access hole to receive the operative instrument. Throughout this process of initially forming an access hole and ultimately inserting an operative instrument through the hole, both zero seals and instrument seals are formed to maintain the pneumoperitoneum.

With the advantages associated with 1) the formation of an instrument seal and a zero seal with a single valve accommodating a wide range of diameters, and 2) the formation of an instrument opening using the instrument itself, it will be appreciated that the concept of this invention will typically be embodied with a structure that is particularly dependent upon the material which forms the access device 34. In a preferred embodiment, the pad 35 is formed of a KRATON/oil mixture including a KRATON Tri-block with a Styrene-Ethylene/Butylene-Styrene (S-E/B-S) structure in combination with a mineral oil. Other tri-block polymers can be used for this application such as Styrene-Isoprene-Styrene, (S-I-S), Styrene-Butadiene-Styrene (S-B-S), Styrene-Ethylene/Propylene-Styrene (S-E/P-S) manufactured under the trademark SEPTON by the Kuraray Co. These general formulas can be further distinguished by the ratio of the styrene to rubber content: for example, Grade 1650 is a S-E/B-S tri-block with a 29/71 styrene to rubber ratio.

In addition to tri-blocks there are also di-block versions of these materials where styrene is present at only one end of the formula, for example, Styrene-Ethylene/Butylene (S-E/B) di-block.

The various base formulas may also be alloyed with one another to achieve a variety of intermediate properties. For example KRATON G1701X is a 70% S-E/B 30% S-E/B-S mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the material of the pad 35 may also include silicone, soft urethanes and even harder plastics which might provide the desired sealing qualities with the addition of a foaming agent. The silicone materials can be of the types currently used for electronic encapsulation. The harder plastics may include PVC, Isoprene, KRATON neat, and other KRATON/oil mixtures. In the KRATON/oil mixture, for example, oils such as vegetable oils, petroleum oils and silicone oils might be substituted for the mineral oil. In the broadest sense, all of these mixtures can be described generally as a gel. The gel will typically have properties including an ability to "flow" which approaches that of a fluid. Particularly in the vicinity of any opening or slit 45 extending through the access device 34, propagation of the opening may be of concern. Stresses resulting from the presence of an instrument will be concentrated at the ends of such an opening or slit. For this reason, a good tear resistance is desired for the gel material. Such a tear resistance is often inherent in the KRATON/oil mixtures and may be enhanced by encapsulating the gel in other materials. For example, a low tear resistant gel could be encapsulated in a urethane sheath to improve the tear resistant qualities of the resulting products. Such a sheath need not be elastic but could be comprised, for example, of overlapping sheets of a non-elastic material.

Any of the gel materials contemplated could be modified to achieve different properties such as enhanced lubricity, appearance, and wound protection, or to provide anti-cancer or anti-microbial activity. Additives can be incorporated directly into the gel, for example in the case of pharmaceuticals, or applied as a surface treatment to the gel, for example, to improve lubricity or appearance. Other compounds could be added to the gel to modify its physical properties or to assist in subsequent modification of the surface by providing bonding sites or a surface charge. Antioxidants and antirads can be added to the mixture to extend the shelf life of the finished product or increase its ability to withstand radiation sterilization.

Sealing materials used in medical access devices of the past have been chosen primarily for their durometer and elongation. It is these properties which measure the ability of the material to move into small spaces and crevices as may be required to form an instrument seal across the working channel of a trocar. For example, in the past, a silicone mixture was used in medical valves. This mixture had the following properties: an ultimate elongation less than about 1000 percent and a durometer not less than about 5 Shore A.

These properties of the prior art materials are far exceeded by the properties associated with the present invention which in some respects provide a full magnitude of advantage. In fact, the difference between the materials of the prior art and the materials of the present invention are sufficiently substantial, that it is perhaps misleading to refer to the present material as merely a gel. According, the material of the present invention, having properties including an ultimate elongation greater than about 1000 percent and a durometer less than about 5 Shore A, will be referred to herein as an "ultragel."

In a preferred embodiment of the present invention, the ultragel includes KRATON and mineral oil and provides a sealing material with the following properties: an ultimate elongation exceeding about 1500 percent, and a durometer of less than about 200 Bloom. The durometer in this case is considerably lower than that of the prior art materials. In fact, the durometer of the present material is so soft it cannot even be measured on the Shore A scale.

The resulting elongation and durometer of the present material facilitates its use with as an access valve which is capable of forming seals with a full range of instrument sizes, but is also capable of functioning as a zero seal. Whereas access devices of the prior art may have required as many as six separate seals in order to accommodate a full range of instrument sizes, access devices can now be made with only a single valve formed of the ultragel material.

In a typical manufacturing process, the KRATON G1651 is mixed with the mineral oil in a ratio by weight of 1 to 9. In order to manufacture this material, the combination is heated to a temperature of about 200° centigrade. In a preferred method of manufacturing, the mold is provided with a circumferential ring insert which is molded into the gel, and slit inserts which can be removed from the gel to form the opening or slit 45. The resulting gel can be coated with cornstarch to reduce tack and cooled at room temperature.

Many of the properties of the KRATON/oil mixture will vary with adjustments in the weight ratio of the components. In general, the greater the percentage of mineral oil, the more fluid the mixture; the greater the percentage of KRATON, the more rigid the material. Weight ratios of KRATON to oil as low as 1 to 5 have been contemplated for a more rigid structure. As the KRATON/oil weight ratio approaches 1 to 10, the mixture becomes more liquid. Ratios as high as 1 to 15 have been contemplated for this invention.

The processing temperature can also vary considerably as it is primarily dependent on the type of KRATON used. Temperatures in a range of about 150° centigrade to about 250° centigrade have been contemplated.

With an appreciation that these ratios and temperatures can develop considerably different properties, it is now apparent that these materials can be layered to provide generally different properties within each layer. For example, an outer layer might be formed of a KRATON/oil mixture having more rigid properties, thereby providing the pad 35 with an outer layer that is more rigid. After that layer is at least partially cured, another layer of the material can be poured inside of the outer layer. This second layer might be softer providing the pad 35 with the significant sealing properties. It has been found that successive layers will tend to fuse slightly at their interface, but will generally maintain their separate identities. Additional layers could be added to provide a progression of properties in a particular device.

Having discussed the properties desirable for the gel material, and the process of manufacture, one can now address the other embodiments of the concept which may provide additional advantages for particular surgical procedures. An embodiment of the access device 34, shown in its operative position in FIG. 6, is illustrated by itself in the axial cross section view of FIG. 8, wherein the access seal with flanges is formed monolithically.

This same embodiment can be reinforced with o-rings 61 and 63 as illustrated in FIG. 9 where elements of structure are designated by the same reference number followed by the lower case letter "b." Providing these o-rings 61 and 63 may facilitate several functions associated with the access device 34b. For example, the rings 61, 63 will typically aid in maintaining a radial sealing pressure on all sides of the opening 45b. The rings 61 and 63 will also tend to maintain the flanges 54b and 56b respectively, in their generally planar configurations. This further ensures that the flanges 54, 56 will not collapse into the incision 32 with the insertion or withdrawal of an instrument, such as the surgeon's hand 17. Of course, the o-rings 61 and 63 must be sufficiently large to accommodate the instrument during insertion and removal.

A further embodiment of the invention is illustrated in FIG. 10, where elements of structure are similar to those previously disclosed are designated with the same reference numerals followed by the lower case letter "c." This embodiment includes the pad 35c with the opening or slit 45c. The external perimeter o-ring 61c is inserted molded into the circumference of the pad 35c. The internal o-ring 63c is coupled to the pad 35c, for example, by way of attachment to the o-ring 61c for example, by a membrane 65. In this case, the membrane 65 has a generally cylindrical configuration and elastomeric properties. In preferred embodiments, the membrane 65 is formed of urethane, neoprene or isoprene.

When the embodiment of FIG. 10 is being operatively positioned, the internal o-ring 63b is initially gathered and inserted through the incision 32 (FIG. 2). The pad 35c and external o-ring 61c are left outside the incision 32 so that the only material extending across the incision 32 is the membrane 65. It will be noted that in this case, the working channel 36c is formed by the slit 45c, the cylindrical membrane 65, and the internal o-ring 63c.

In this particular embodiment, the pad 35c functions generally as described with reference to FIG. 2. The primary seal between the pad 35c and the abdominal wall 21 can be formed either with a circumferential ring, such as the adhesive ring 52c, or by relying on the sealing characteristics of the insufflation gas 58c against the internal o-ring 63c and membrane 65.

This embodiment of FIG. 10 is of particular advantage as it incorporates the pad 35c in perhaps its simplest configuration, while providing a primary seal between the device 34c and the abdominal wall 21 which is facilitated by the insufflation pressure. Furthermore, the membrane 65 enhances the sealing characteristics of the device 34c, and provides a lining for the incision 32. With the membrane 65, the incision 32 need not be stretched to a diameter greater than that required by any instrument inserted through the working channel 36c.

Figure 8:
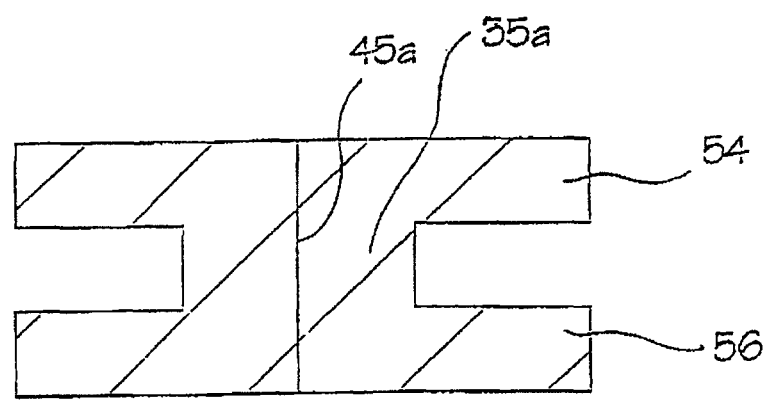
FIG. 8 is an axially cross section view of the access device illustrated in FIG. 6.

A further embodiment of the invention is illustrated in FIG. 11 where elements of structure similar to those previously disclosed are designated with the same reference numeral followed by the lower case letter "d." This embodiment is similar to that of FIG. 8 in that it includes the pad 35b, slit 45d, exterior flange 54d, and internal flange 56d. The embodiment of FIG. 11 differs from that of FIG. 8 in that it includes a lead-in cavity 70 which is in communication with the slit 45d.

In a preferred embodiment, this cavity 70 is sized and configured to receive the arm 16 of the surgeon 14 in a manner illustrated in FIG. 7. In this case, the slit 45d would function primarily to maintain a zero seal, while the portions of the pad 35d or flange 54d which form the cavity 70 would function primarily to form the instrument seal.

Figure 12:
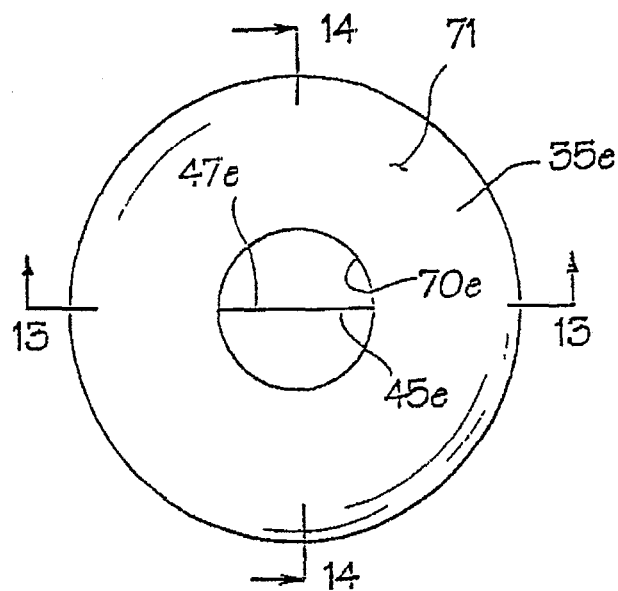
FIG. 12 is a top plan view of the embodiment illustrated in FIG. 11.
Figure 13:
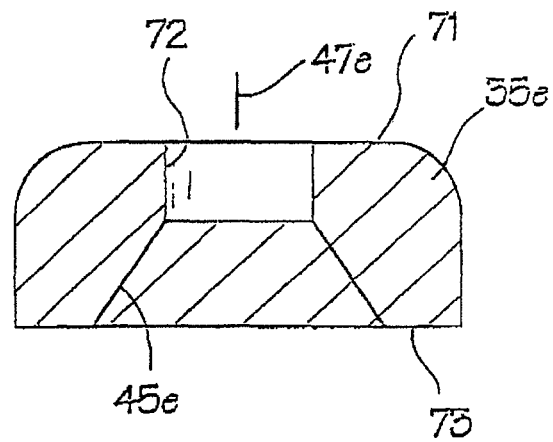
FIG. 13 is an axial cross section view taken along lines 13-13 of FIG. 12.
Figure 14:
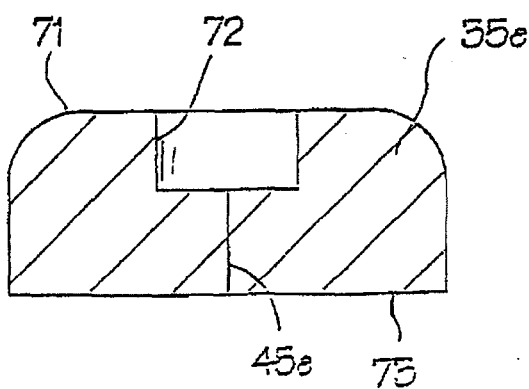
FIG. 14 is an axial cross section view taken along lines 14-14 of FIG. 12.

A further embodiment of the invention is illustrated in the plan view of FIG. 12 and the cross section views of FIGS. 13 and 14. In this embodiment, elements of structure similar to those previously discussed are designated with the same reference numeral followed by the lower case letter "e." In this case, the lead-in cavity has the general shape of a cylinder 72 with an axis that is collinear with the axis 47e of the pad 35e.

As perhaps best illustrated in FIG. 13, the slit 45e has a trapezoidal configuration. Thus, it begins proximally with a narrow length which may generally be equivalent to the diameter of the cylinder 32. From the cavity 70e, the length of the slit 45e increases with progressive positions distally through the pad 35e. In the illustrated embodiment, the trapezoidal slit 45e is formed as the frustum of an isosceles triangle.

Figure 15:
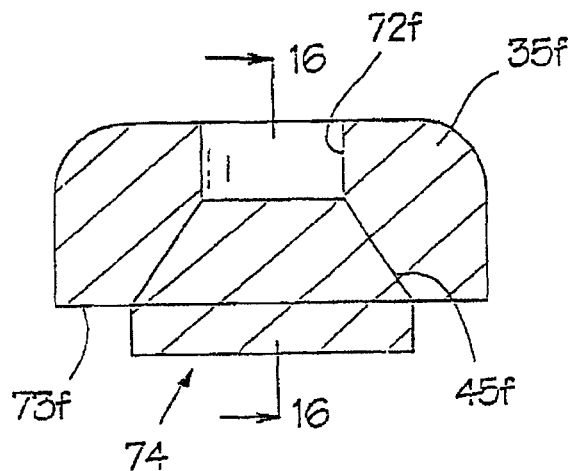
FIG. 15 is an axial cross section view similar to FIG. 13 and illustrating an embodiment with a duct-bill valve.
Figure 16:
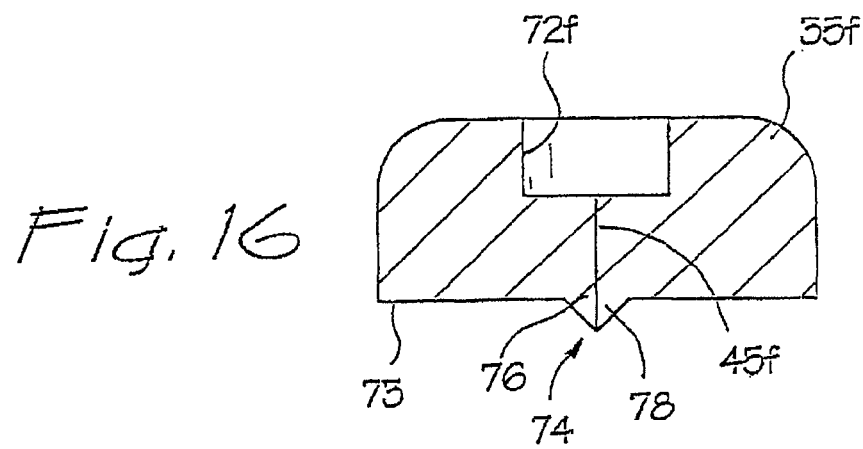
FIG. 16 is an axial cross-section view taken along lines 16-16 of FIG. 15.

A further embodiment of the invention is illustrated in FIGS. 15 and 16 wherein elements of structure similar to those previously described are designated with the same reference numeral followed by the lower case letter "f." As previously discussed with reference to FIG. 12, this embodiment of the pad 35f is formed with a proximal surface 71 and a distal surface 73. The pad 35f also includes the coaxial lead-in cylinder 72f and the trapezoidal slit 45f. However, in this case, a duck-bill valve 74 is provided to further enhance the characteristics of the zero zeal. As illustrated, the working channel 36f is formed by the lead-in cavity 70f, the slit 45f, and an extension of the slit 45f which is defined by the duck-bill valve 74f.

The duck-bill valve 72 can be formed with opposing flanges 76 and 78 which extend distally of the distal surface 73. When operatively disposed, the pad 35f can be positioned with its distal surface 73 against the exterior surface of the abdominal wall 21 (FIG. 2) and with the flanges 76 and 78 extending into the incision 32. With this configuration and operative disposition, the abdominal wall 21 at the incision 32 will produce opposing forces on the flanges 76 and 78 which tend to close the slit 45f, particularly in the absence of an instrument. In this manner, the duck-bill valve 74 can be relied on to enhance the characteristics of the zero seal.

Figure 17:
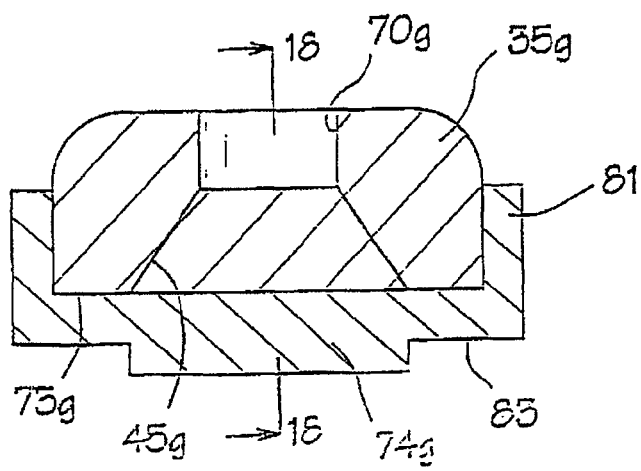
FIG. 17 is a radial cross section view similar to FIG. 13 comprising a softer hand seal and a firmer base seal.
Figure 18:
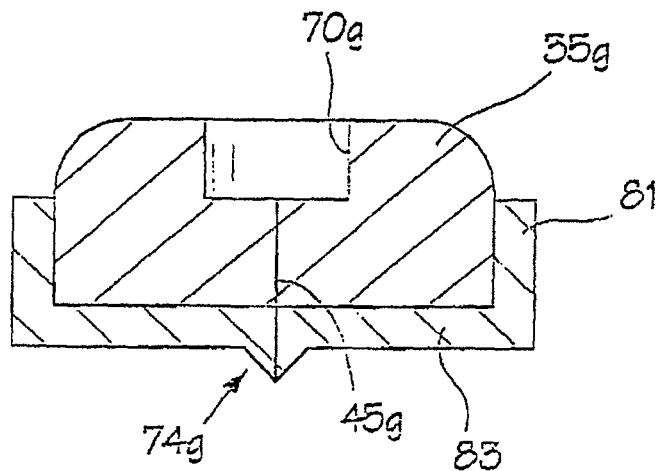
FIG. 18 is an axial cross section view taken along lines 18-18 of FIG. 17.

A further embodiment of the invention is illustrated in FIGS. 17 and 18 wherein elements of structure similar to those previously discussed are designated by the same reference numeral followed by the lower case letter "g." In this embodiment of the access device 34g, the pad 35g can be formed generally as discussed with reference to FIG. 13. In this embodiment, however, the pad 35g can be enclosed along its sides and the distal surface 73g, by a base 81. In this case, the pad 35g might be formed by the highly elastic material previously discussed, while the base 81 might be formed of a more rigid but nevertheless flexible material such as a urethane. With this configuration, the duck-bill valve 74f would be structured to extend distally of a distal surface 83 associated with the base 81. This would enable the duck-bill valve 74f to be formed of the base material rather than the superelastic material. This might also improve the zero seal characteristics for particular operative applications.

Figure 19:
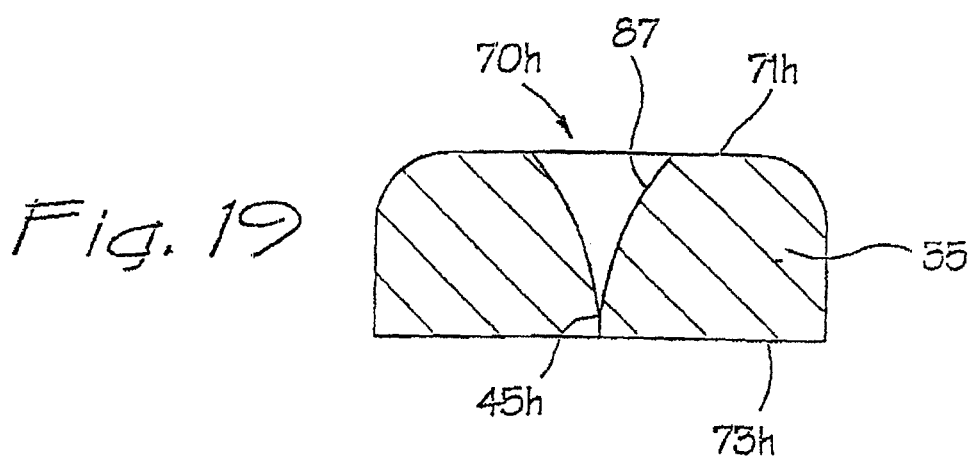
FIG. 19 is an axial cross section view of an embodiment having a lead-in cavity or pocket with a conical or funnel configuration.
Figure 20:
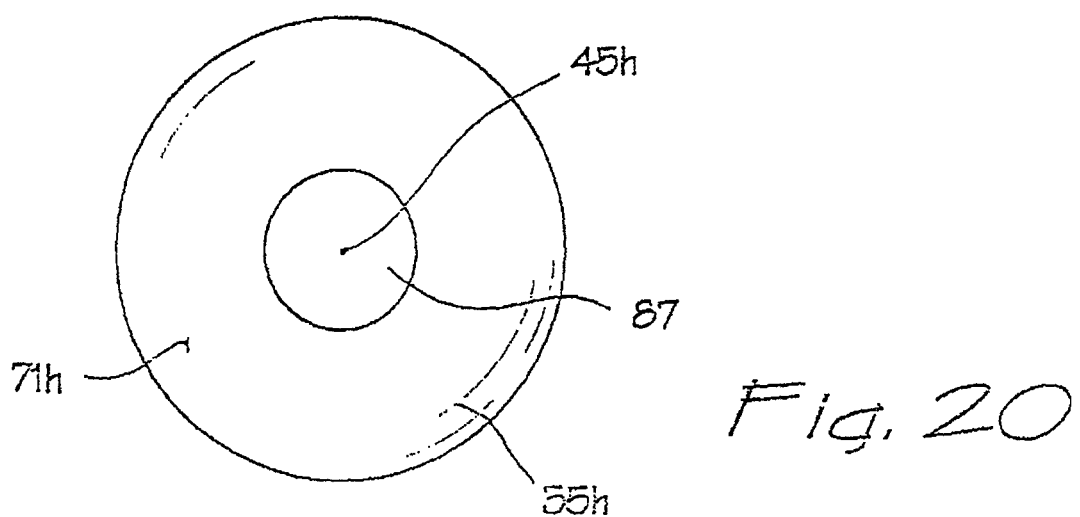
FIG. 20 is a top plan view of the embodiment illustrated in FIG. 19.

Another simplified form of the invention is illustrated in FIGS. 19 and 20, where elements of structure similar to those previously discussed or designated with the same reference numeral followed by the lower case letter "h." The lead-in cavity 78h, in this case, is formed as an inverted cone 77 having its base at the proximal surface 71h and its apex in proximity to the distal surface 73h. Thus, the lead-in cavity 70h has an area in radial cross section which decreases with progressive positions distally through the pad 35h. In this embodiment, the proximal regions near the base of the cone 87 form the instrument seal, while the distal regions at the apex of the cone form the zero seal. The conical configuration of the lead-in cavity 70h also tends to funnel an instrument into the opening 45h leading distally to the apex of the cone 87.

Figure 21:
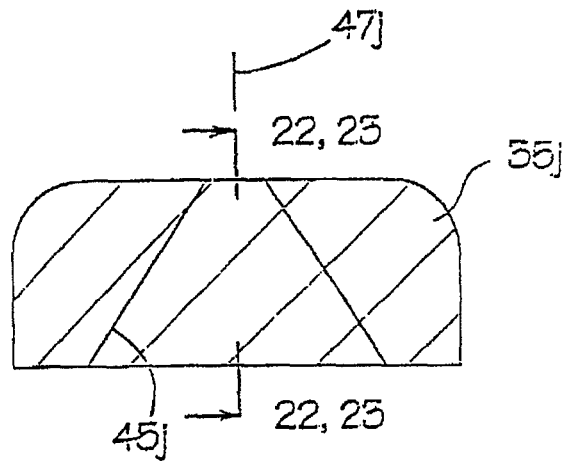
FIG. 21 is an axial cross section view similar to FIG. 13 and showing another embodiment with a trapezoidal slit.
Figure 22:
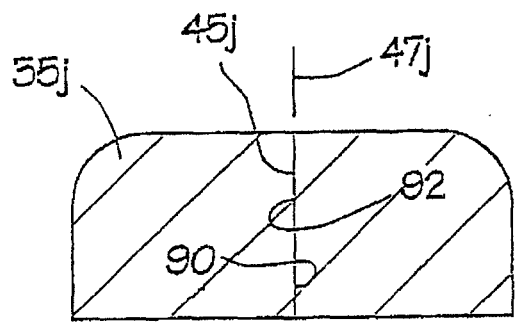
FIG. 22 is an axial cross section view taken along lines 22-22 of FIG. 21.

It will be appreciated generally, that the slit 45 and lead-in cavity 70 can be provided with many different individual and cooperative configurations. By way of example, perhaps the simplest form for the pad 35 is illustrated in the embodiment of FIGS. 21 and 22 wherein elements of structure similar to those previously described are designated by the same reference numeral followed by the lower case letter "j." In this embodiment, the pad 35j with its proximal surface 71j and distal surface 73j, is provided with a simple trapezoidal slit 45j. In this case, the slit 45j extends between the proximal surface 71j and the distal surface 73j.

The slit 45j in this embodiment of FIG. 21 is typical of many structures which will define the slit 45j with a planar configuration. In such a case, the portions of the pad 35j which form the slit will comprise opposing planar surfaces such as those designated by the reference numerals 90 and 92 in FIG. 22.

It will be apparent that the slit 45 need not be formed by opposing surfaces having a planar configuration. Nevertheless, these opposing surfaces need to be capable of coming into sealing contact with each other in order to establish the zero seal. Other slit configurations capable of accomplishing this function, may offer further advantages in particular procedures. Other examples of slit configurations are illustrated merely by way of example in FIGS. 23-26.

Figure 23:
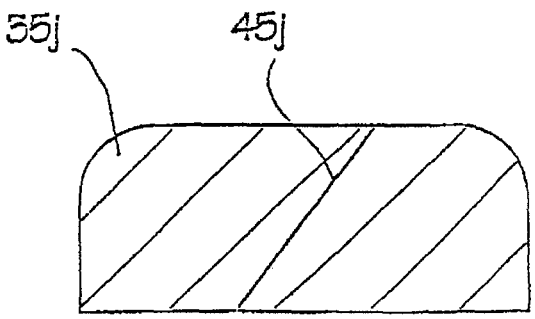
FIG. 23 is an axial cross section view similar to FIG. 22 taken along lines 23-23 of FIG. 21 and illustrating a slit having other than a perpendicular relationship to the plane of the pad.

The embodiment of FIG. 23 is similar to that of FIG. 22 in that the opening 45j comprises a single slit which extends from the proximal surface 71j to the distal surface 73j. In the case of the FIG. 22 embodiment, the axis 47j is disposed within the plane of the slit 45j. In the case of the FIG. 23 embodiment, the plane of the slit 45j does not include the axis 47j. Rather, the slit 45j is formed in a plane which has an angular relationship with the axis 47j, the proximal surface 71j, as well as the distal surface 73j. This construction enables the slit 45j to have a length greater than the thickness of the pad 35j.

Figure 24:
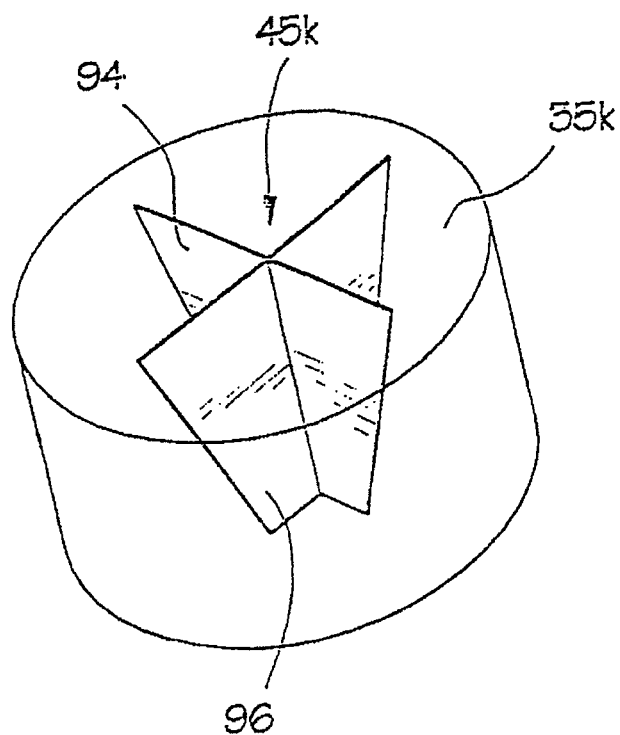
FIG. 24 is a perspective view of a further embodiment of the access device having an opening formed by multiple slits angularly disposed and axially spaced relative to each other.

In the embodiment of FIG. 24, elements of structure similar to those previously discussed are designated with the same reference numeral followed by the lower case letter "k." In this case, the opening 45k is configured as two slits 94 and 96 formed in individual planes that are angularly spaced with respect to each other. Of course, two or more of the planar slits 94 and 96 may be equally angularly spaced around the axis 47k. In one embodiment, the individual planar slits 94 and 96 intersect at the axis 47k. Alternatively, the slits 94 and 96 may be axially spaced in order to facilitate formation of the instrument seal.

Figure 25:
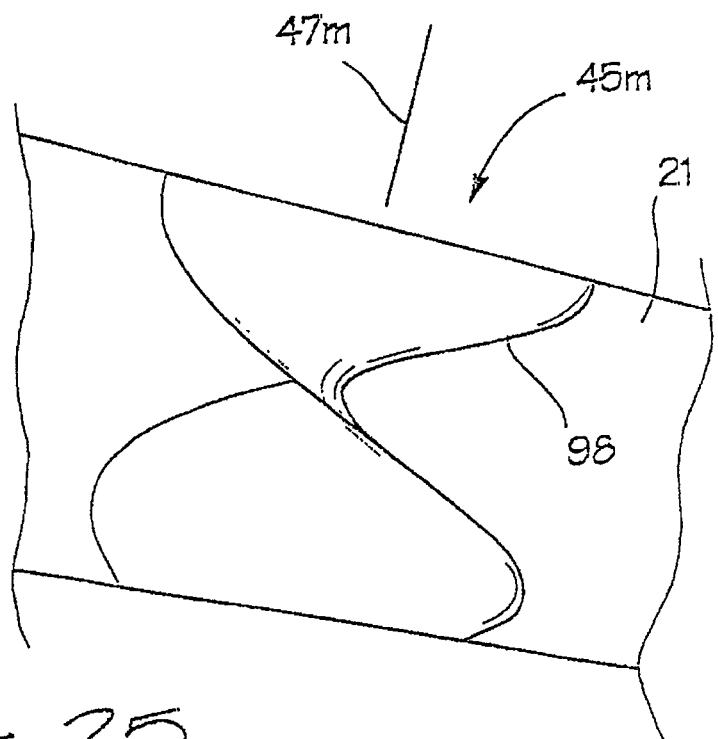
FIG. 25 is a side elevation view of an access device with a slit having a spiral configuration.

In the embodiment of FIG. 25, elements of structure similar to those previously discussed are designated with the same reference numeral followed by the lower case letter "m." In this embodiment, the opening 45m is defined as a slit 98 having a curved rather than planar configuration. In the illustrated embodiment, the curved slit 98 is formed as a spiral around the axis 47m. Along the axis 47m, the opposing surfaces forming the spiral slit 98 can "flow" into sealing proximity in order to produce the zero seal.

Figure 26:
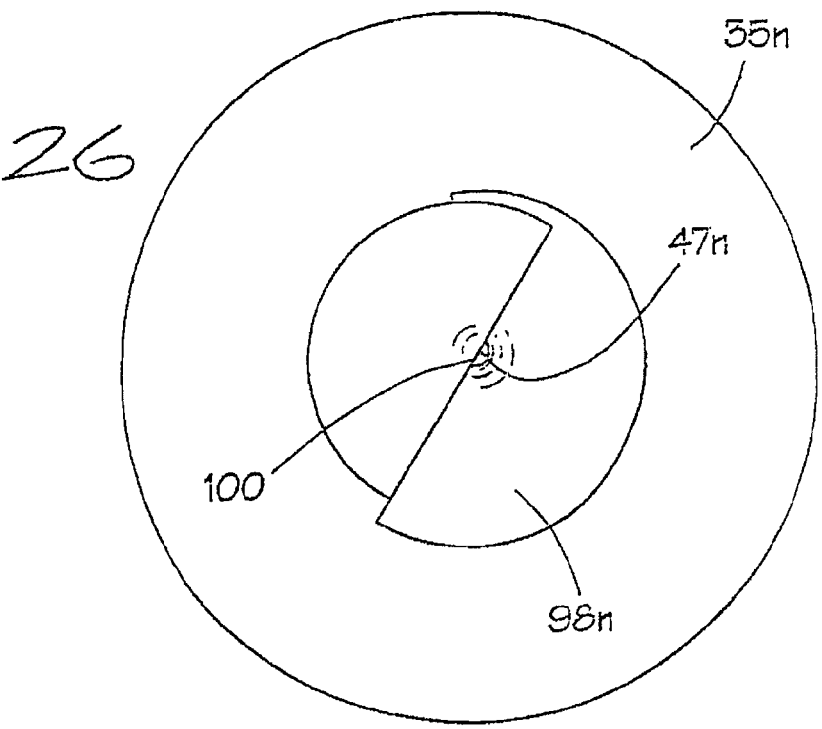
FIG. 26 is a top plan view of an access device having a spiral slit and axial channel.

FIG. 26 illustrates a similar embodiment including a spiral slit. In this figure, elements of structure similar to those previously discussed are designated by the same reference numeral followed by the lower case letter "n." The spiral slit 98n in this embodiment is also formed around the axis 47n of the pad 35n, but in this case the portions forming the slit 98n do not extend completely to the axis 47n. As a result, an axial channel 100 is formed at least partially along the axis 47n. This channel 100 can function in a manner similar to the lead-in cavity 70 discussed with reference to FIGS. 11-12. This channel 100 can even be formed with a conical configuration similar to that discussed with reference to FIG. 19.

Figure 27:
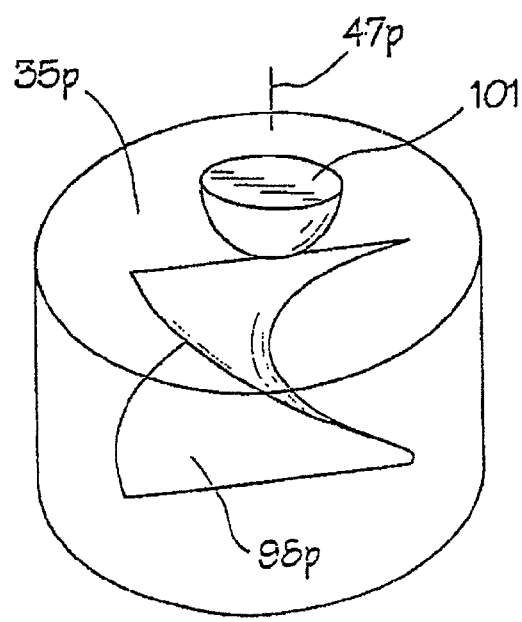
FIG. 27 is a side elevation view of an embodiment having a spiral slit and a septum seal.

In an embodiment where the channel 100 is left open, a zero seal might be provided by positioning a septum valve across the channel 100. Such an embodiment is illustrated in FIG. 27, wherein the septum valve is designated with a reference numeral 101 and the other elements of structure similar to those previously discussed are designated with the same reference numerals followed by the lower case letter "p." Thus the embodiment of FIG. 27 includes the spiral slit 98p, the pad 35p, and the axis 47p. This embodiment of FIG. 27 is merely representative of many other embodiments that will combine a slit, such as the slit 98p, with other valve structures, such as the septum valve 101.

Other curved slit configurations would include embodiments wherein the slit is curved, sinusoidal, or S-shaped in a side elevation view. Such configurations provide a slit part having a length greater than the thickness of the pad. Normally, the more circuitous the slit path, the better the sealing characteristics.

Figure 28:
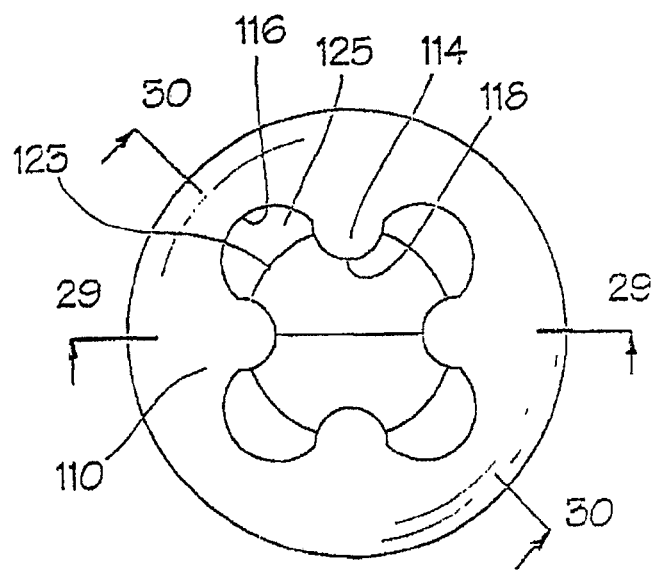
FIG. 28 is an axial cross section view of a further embodiment including a superelastic conical seal and a flexible base with annular spoke-like cams.
Figure 29:
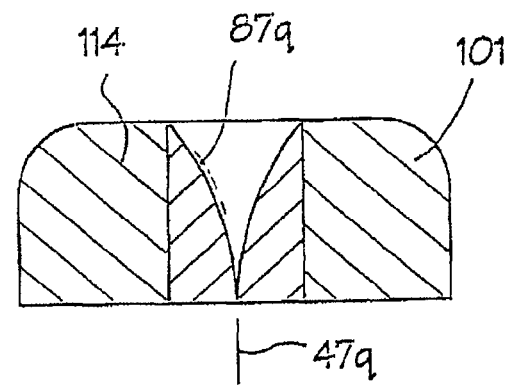
FIG. 29 is an axial cross section view taken along lines 29-29 of FIG. 22.
Figure 30:
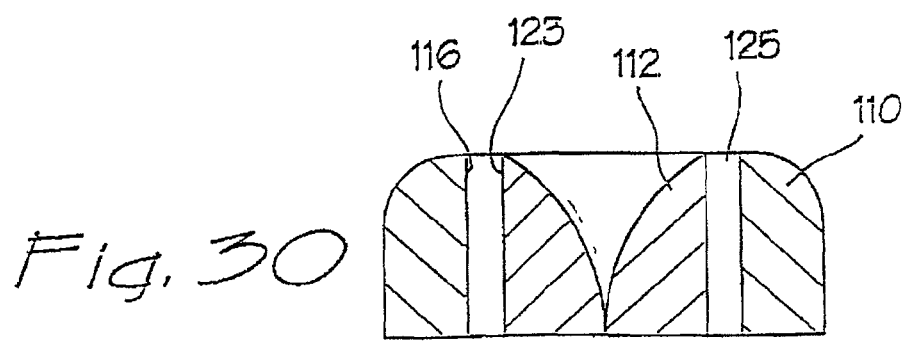
FIG. 30 is an axial cross section view taken along lines 30-30 of FIG. 22.

A further and more complex configuration for the opening 45 is illustrated in the embodiment of FIG. 28 wherein elements of structure similar to those previously disclosed are designated with the same reference numeral followed by the lower case letter "q." This embodiment is representative of many other complex embodiments which can be formed with intricate shapes and different materials in order to accomplish the desirable function of forming, with a single valve, a zero seal as well as an instrument capable of accommodating a full range of instrument sizes. In the embodiment of FIG. 28, the pad 35q is formed with a base 110 which is disposed circumferentially of a core 112. In this case, the core 112 is formed of the superelastic material or gel and provided with the shape of the cone 87q as discussed with reference to FIGS. 19 and 20. The base 110 is formed from a material that may not be elastic, but preferably is flexible. In the preferred embodiment, the base 110 is formed of a urethane.

In this construction, the base 110 is provided with a plurality of spokes 114 each of which extends radially inwardly from a base 116 to a tip 118. The core 112 extends from the axis 47q outwardly to the tips 118 of the spokes 114. In the illustrated embodiment, the core 112 has fingers 121 which extend beyond the tips 118 and toward the bases 116 between each adjacent pair of the spokes 114. These fingers 121 extend radially outwardly to an end surface 123 which stops short of the base 116 leaving a void 125 therebetween.

The voids 125 are of particular interest to this embodiment and can be incorporated into any of the embodiments previously discussed. Such voids 125 provide a space or absence of material into which the highly elastic material, such as that of the fingers 121, can expand during insertion of an instrument such as the arm 16 (FIG. 7). Since the gel material is almost fluid in its properties, the voids 125 permit expansion of the gel with very little resistance. Voids, such as the voids 125 in the embodiment of FIG. 28, can be defined solely in the gel material or between the gel material and any other base material.

Figure 31:
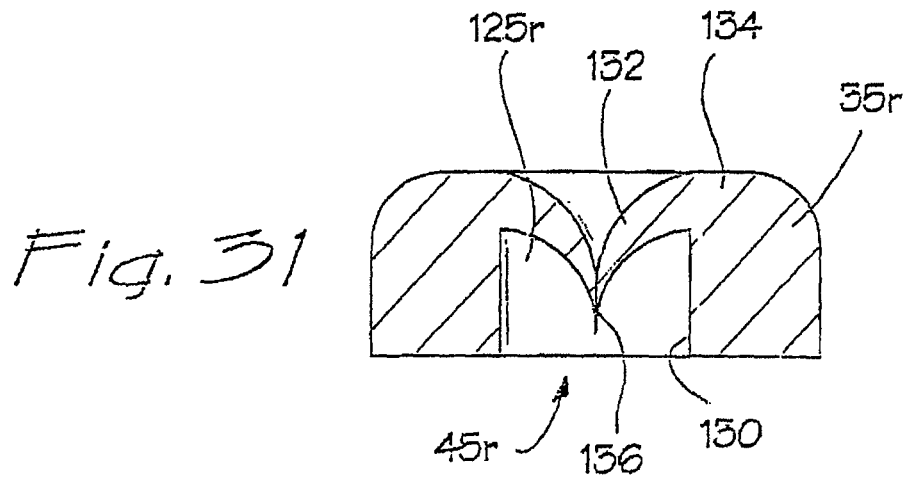
FIG. 31 is an axial cross section view similar to FIG. 28 and illustrating an embodiment including flappers.

In the case of FIG. 28, the spokes 114 and fingers 121 are defined generally in planes which are parallel to the axis 47q. Similar fingers, illustrated in the embodiment of FIG. 31 are defined generally in a plane which is perpendicular to the axis. In this embodiment, elements of structure similar to those previously disclosed are designated by the same reference numeral followed by the lower case letter "r." As illustrated, the pad 35r can be formed with a relatively large opening 45r having the configuration of a coaxial cylinder 130. A plurality of fingers or flaps 132 extend into the opening 45r and tend to form a lead-in cavity 70r with properties such as those discussed with reference to FIG. 19. In this case, the annular flaps 132 have a conical configuration extending from a base 134 to an apex 136. It will be noted that the areas between the flaps 132, form voids 125r into which the flaps 132 can be displaced upon insertion of an instrument, such as the arm 16.

Figure 32:
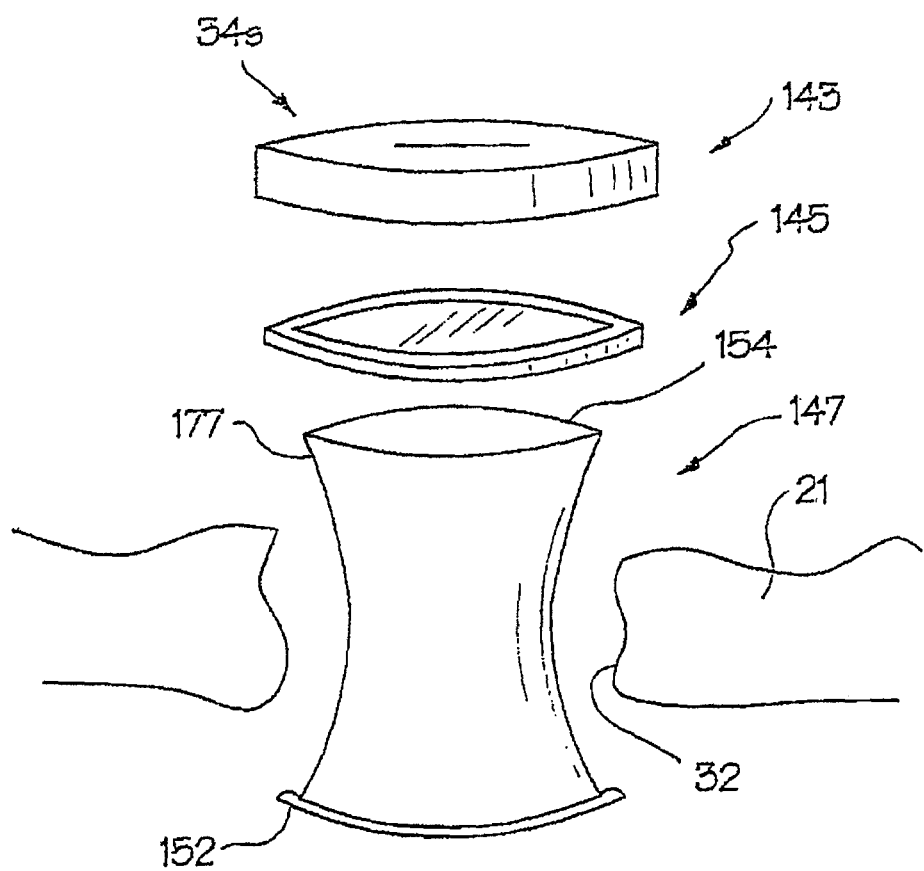
FIG. 32 is a perspective exploded view of a further embodiment including a gel cap, a base, and a retraction sheath.

A further embodiment of the invention is illustrated in FIG. 32 where elements of structure similar to those previously disclosed are designated with the same reference numeral followed by the lower case letter "s." This exploded view of the access device 34s includes not only the pad 35s but also a complimentary structure for maintaining the position of the pad 35s, for forming a seal between the pad 35s and the abdominal wall 21, and for dilating the incision 32 to a variable extent as required by the surgeon 14. In this case, the access device 34s includes three components, a gel cap 143, base 145, and a retraction sheath 147.

The gel cap 143 includes not only the gel pad 35s, but also a circumferential cap ring 154 which can be inserted and molded to the pad 35s. The resulting gel cap 143 forms a seal with the base 145, thereby defining the working channel 36s through the pad 35s, the cap ring 154, the base 145, and the retraction sheath 147. In the manner previously discussed, this working channel 36s includes the single valve formed by the gel pad 35s which provides both a zero seal and an instrument seal for a wide range of instrument diameters.

Figure 33:
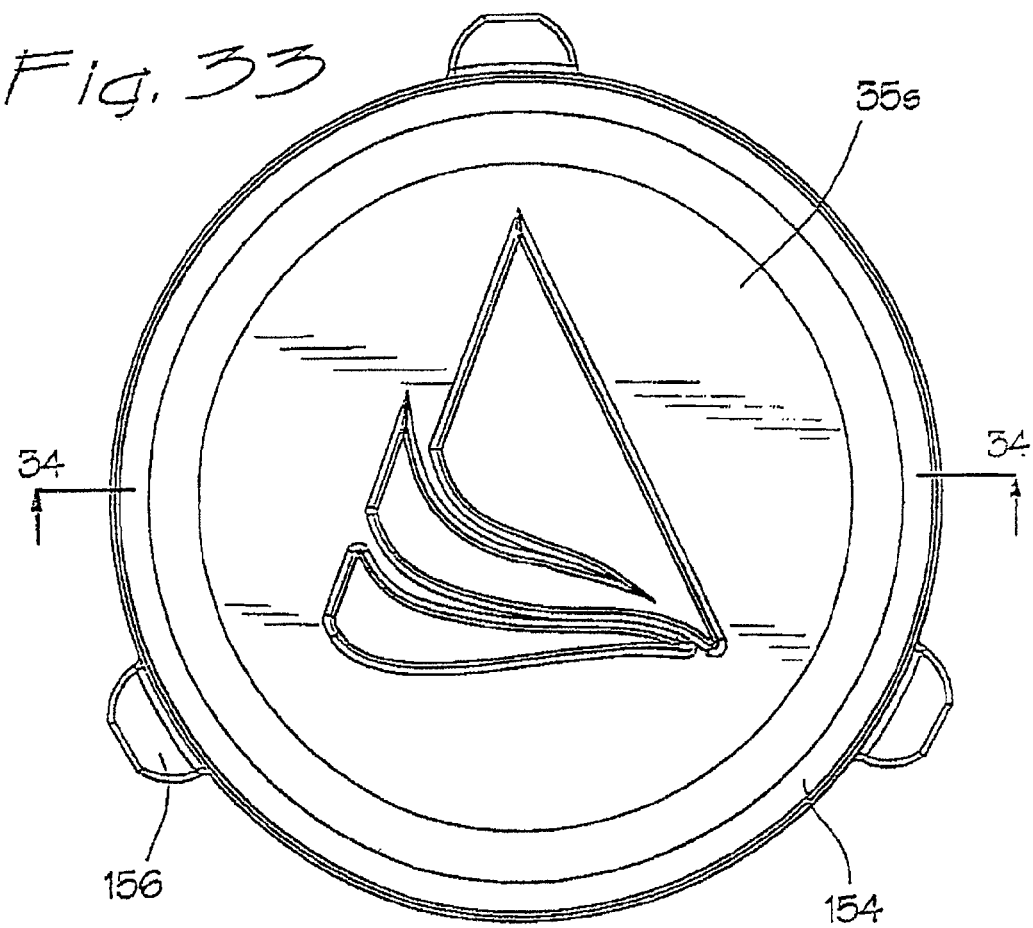
FIG. 33 is a top plan view of the gel cap of FIG. 32.

The structure associated with the gel cap 143 is described in greater detail with reference to FIGS. 33 and 34. In the plan view of FIG. 33, it can be seen that this embodiment includes the gel pad 35s centrally disposed within the circumferential cap ring 154. Holding tabs 156 can be provided to extend radially outwardly of the cap ring 154. These holding tabs 156 can facilitate the sealing engagement of the gel cap 143 with the base 145 in the manner described in greater detail below.

The gel pad 35s can be formed of any of the materials previously discussed although the preferred embodiment includes the KRATON/mineral oil gel. The cap ring 154 for such an embodiment can be advantageously formed of KRATON only. This will make the cap ring 154 more rigid than the gel pad 35s while maintaining an excellent material interface between the pad 35s and the ring 154. In a typical manufacturing operation, the cap ring will be pre-disposed in the mold for the gel pad 35s with the unitary structure of the gel cap 143 resulting.

Figure 34:
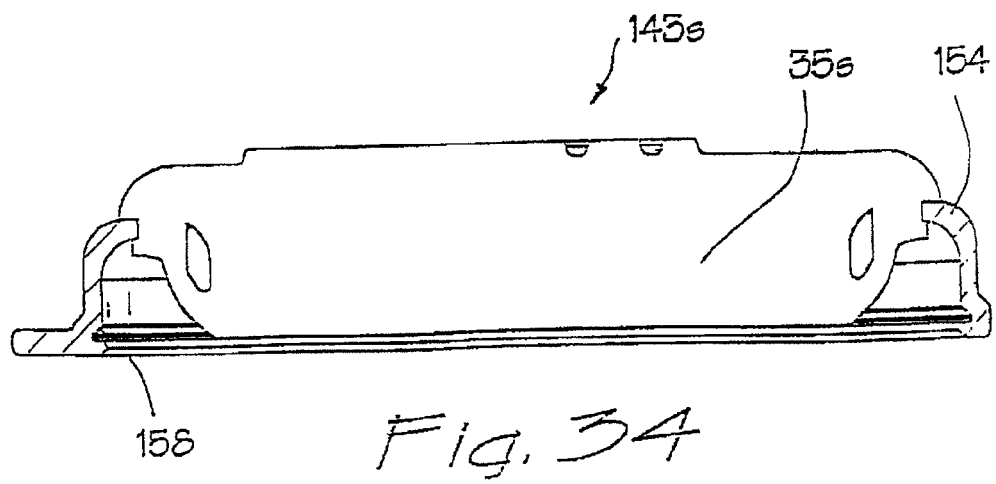
FIG. 34 is an axial cross section view taken along lines 34-34 of FIG. 33.

The cross section view of FIG. 34 shows the gel cap 143s and illustrates an annular void 158 formed on the inner circumference of the cap ring 154. This void 158 is of particular advantage in forming a sealing relationship with the base 145 in the manner discussed in greater detail below.

Figure 35:
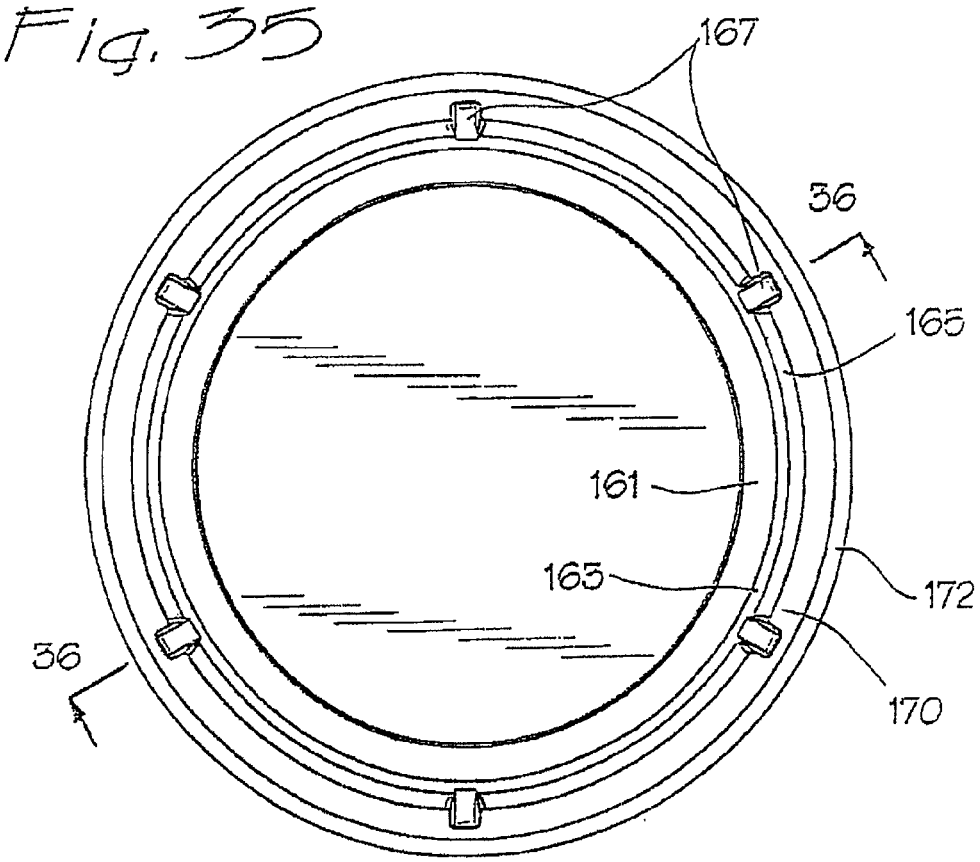
FIG. 35 is a top plan view of the base illustrated in FIG. 32.

The base 145 of this embodiment is shown in greater detail in the plan and cross section of views of FIGS. 34 and 35, respectively. From these views it will be noted that the base 145 can be provided with a smooth generally cylindrical inner surface 161 which extends proximally to a rounded end surface 163 and outwardly from the end surface 163 along an annular lip 165. A plurality of tabs 167 can be equally spaced to extend outwardly and distally around the circumference of the lip 165.

Distally of the inner surface 163, an annular flange 170 can be provided with an annular projection 172 sized and configured to form the desired sealing relationship between the gel cap 143 and the base 145. The process of molding the base 145 can be facilitated by forming the base as two separate components divided, for example, by a dotted line 174 in FIG. 35. In a preferred embodiment, the base 145 is molded from a polycarbonate material.

Figure 37:
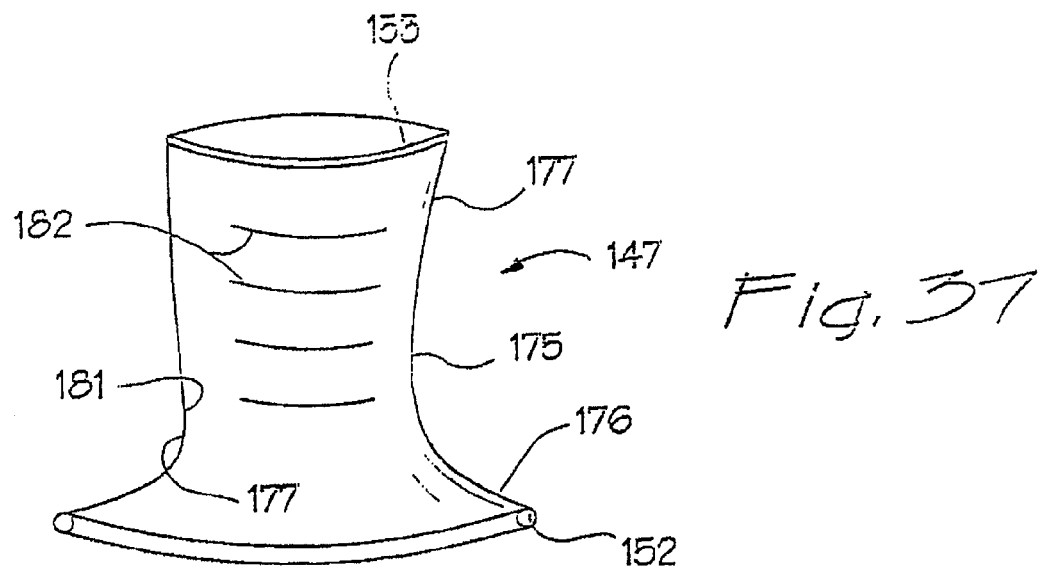
FIG. 37 is a side elevation view of the retraction sheath illustrated in FIG. 32.

A preferred embodiment of the retracting sheath 147 is illustrated in FIG. 37. In this view it can be seen that the retraction sheath 147 includes a tubular wall 175 which has the configuration of the frustum of a cone 176 at its distal end and the configuration of a cylinder 177 at its proximal end. A flexible retaining ring 152 terminates the distal end while a fold 154 is formed at the proximal end. The tubular wall 175 is illustrated to include an outer surface 180 and an inner surface 181. In a preferred embodiment, the sheath 147 is formed of an elastomer, such as neoprene, so its frustule conical and cylindrical configurations exist primarily in the natural unstretched state.

As the sheath 147 is stretched axially, the diameter of the cylindrical proximal end increases thereby placing radial forces on the incision 32. The more the sheath 147 is stretched axially, the greater becomes the diameter of the sheath and consequently the larger becomes the opening through the incision 32. This feature is of particular advantage as it permits the surgeon to define the size of the incision 32 with an appropriate degree of axial tension on the sheath 147. By maintaining this tension, the preferred size of the incision 132 is maintained throughout the operation. In a preferred apparatus and method, the axial tension is maintained by stretching the sheath 147 over the tabs 167 (FIG. 34) of the base 145. Indicia 182 can be printed on the sheath 147 to provide an indication of the relationship between the axial stretch of the sheath 147 and the size of the incision 32.

Figure 38:
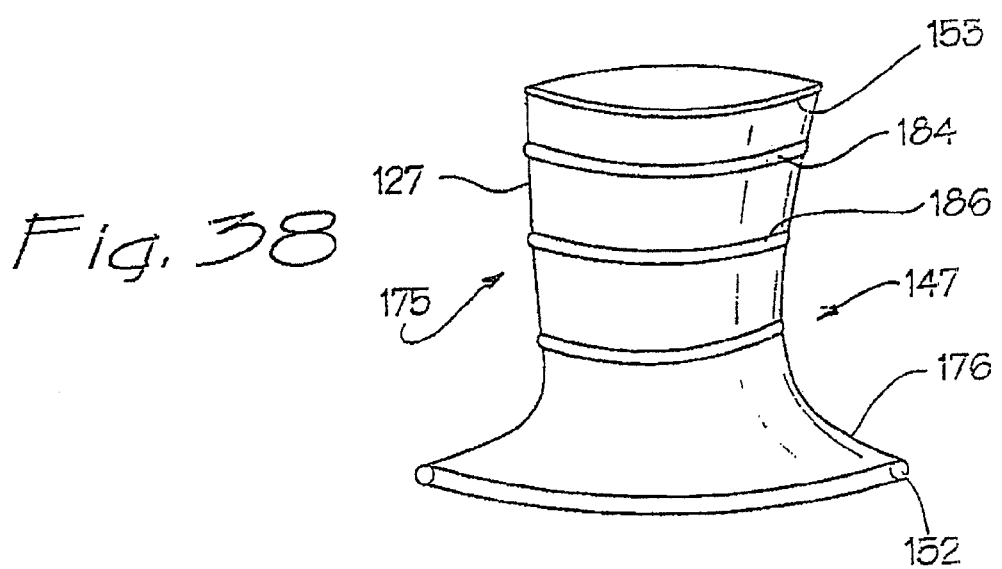
FIG. 38 is a side elevation view of a further embodiment of the retraction sheath.

The fold 153 is provided to facilitate a grip on the proximal end of the sheath 147. This fold 153 can also function to provide reinforcement where the walls of the sheath 147 engage the tabs 167 of the base 145. In the embodiment illustrated in FIG. 38 additional folds 184, 186 are provided at spaced axial locations, such as those defined by the indicia 182 in FIG. 37. With these folds 184 and 186, additional points of reinforcement are provided to engage the tabs 167 while providing the sheath 147 with predetermined degrees of axial stretch associated with different sizes of the incision 32.

Figure 39:
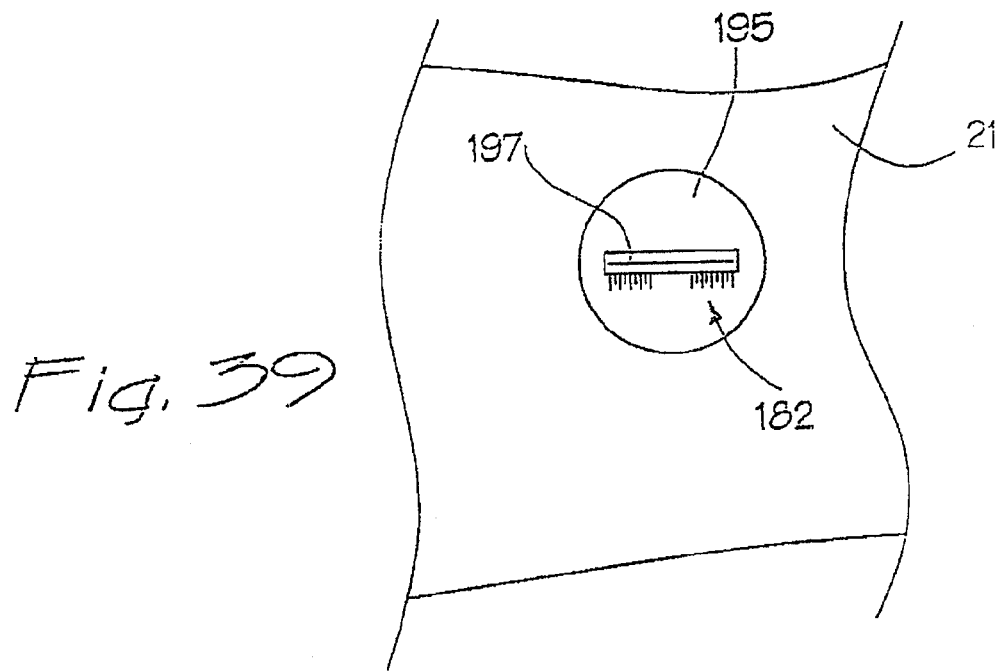

The method of using the embodiment of FIG. 32 is illustrated the progressive use of FIGS. 39-42. In FIG. 39, a top plan view of the abdominal wall 21 of the patient 10 is illustrated with a template 195 positioned to facilitate location of the incision 32. The size of the incision 32 can be determined with the indicia 182 on the template 195 showing, for example, multiple lengths of a line 197, each length being equated with a glove size for the surgeon's hand 17 (FIG. 7). Knowing his/her glove size, the surgeon will merely cut the incision in accordance with an appropriate length of the line 197. The longer lengths of the line 197 are associated with the larger incisions, the larger glove sizes and accordingly the larger hands 17. After the incision 32 has been cut along the line 197, the template 195 can be removed.

Figure 40:
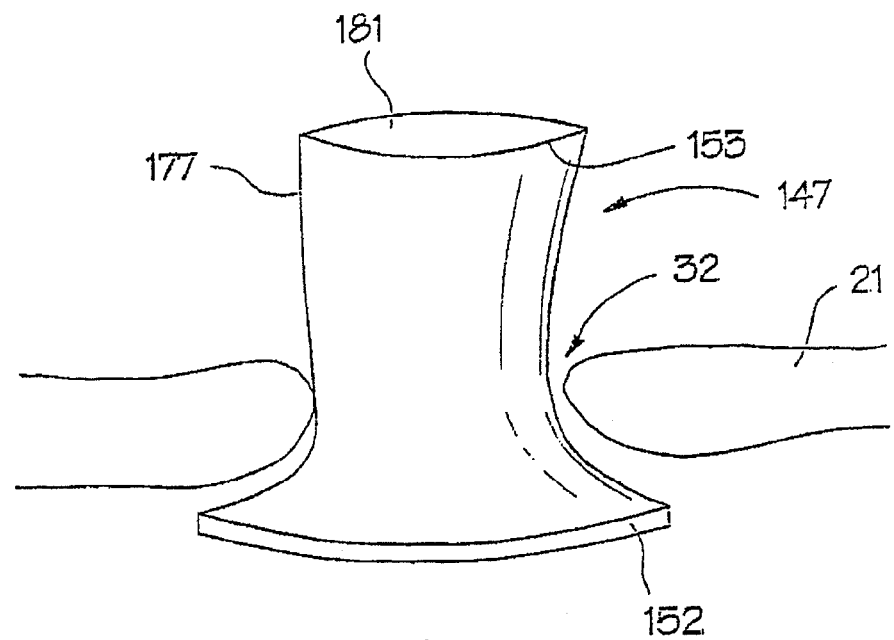

As illustrated in FIG. 40, the retraction sheath 147 can then be mounted through the incision 32. Initially the ring 152 is compressed and fed through the incision 32. On the inner surface of the abdominal wall 21, the ring 152 is free to expand to its larger diameter, as shown by a dotted line 158 in FIG. 40. The portions of the wall 176 which define the cylinder 177 are left to extend proximally through the opening 32 as shown in FIG. 40.

Prior to or after inserting the sheath 147, the base 145 can be disposed around the incision 32. Then the exposed portions of the sheath 147 will extend through the incision 32 and within the circumferential base 145. As illustrated in FIG. 41, the wall 176 of the sheath 147 can then be drawn proximally, outwardly of the page in FIG. 41, to axially stretch the sheath 147. As noted, when the sheath 147 is axially stretched, it will create radial forces on the abdominal wall 21 which will tend to enlarge the incision 32. The greater the axial stretch, the larger the incision 32.

Figure 36:
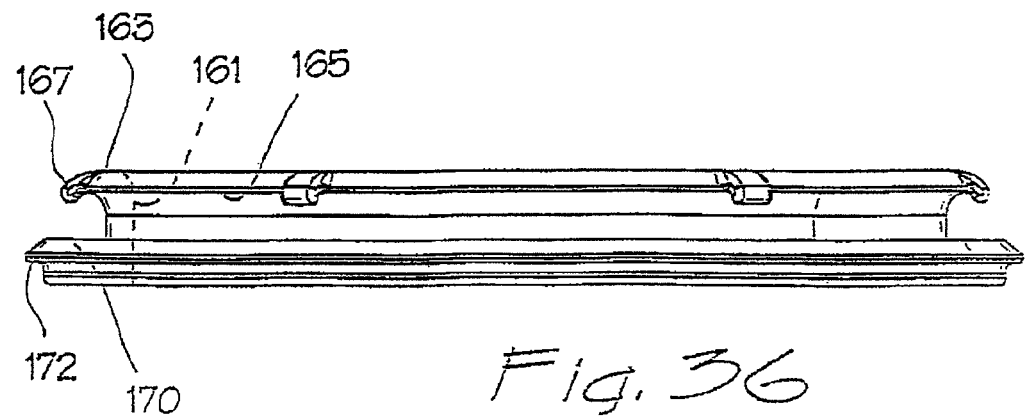
FIG. 36 is an axial cross section view taken along lines 36-36 of FIG. 35.

When the incision 32 has the desired size, the stretched sheath 147 can be drawn over the tabs 167 to maintain the axial stretch and the desired size for the incision 32. Either the indicia 182, as shown in FIG. 36, or the additional folds 184 and 186 as shown in FIG. 37, can be aligned with the tabs 167 to provide a predetermined size for the incision 32. At this point, the seal between the abdominal wall 21, the sheath 147, and the base 145 is fully established.

A final step remaining in this process is the attachment of the gel cap 143 to the base 145. This is accomplished as illustrated in FIG. 36 by, capturing the lip 172 of the base 145 in the annular void 158 of the gel cap 143. Bending the holding tabs 156 upwardly and outwardly facilitates this engagement which ultimately forms a seal between the base 145 and the gel cap 143.

Although this invention has been disclosed with reference to certain structural configurations, it will be appreciated that these products are merely representative of many different embodiments of the invention. Accordingly, one is cautioned not to limit the concept only to the disclosed embodiments, but rather encouraged to determine the scope of the invention only with reference to the following claims.

What is claimed is:

1. A surgical access device, comprising:
a non-inflatable access port sized to span a thickness of an abdominal wall of a patient and adapted to permit access of at least one surgical instrument through an incision in the abdominal wall of the patient and into an abdominal cavity, wherein the access port comprises a proximal portion, a distal portion, and an intermediate portion between the proximal portion and the distal portion, wherein an opening extends through the access port between the proximal portion and the distal portion, and
a surgical instrument, wherein the surgical instrument is a trocar having a valve structure configured to inhibit the escape of gas through the trocar when in use in an operative position,
wherein the proximal portion comprises a proximal flange having a proximal flange diameter, wherein the proximal portion has a proximal surface portion and a distal surface portion, wherein the proximal surface portion at least partially defines a concave area,
wherein the distal portion comprises a distal flange having a distal flange diameter,
wherein the proximal flange, the distal flange, and the intermediate portion are monolithically formed of an elastomeric material, wherein the intermediate portion comprises an outer surface and at least one inner surface, the outer surface has a diameter that is less than the proximal and distal flange diameters, the inner surface at least partially defines the opening, and
wherein the access port is sized and adapted to be disposed within the abdominal wall in an operative position, wherein disposition of the access port within the abdominal wall maintains the access port in the operative position and forms a perimeter seal between the outer surface and the abdominal wall when the intermediate portion is disposed across the incision and positioned within the incision with the proximal flange disposed exteriorly of the abdominal wall and the distal flange disposed interiorly of the abdominal wall, and wherein the access port is adapted to form a seal with the surgical instrument positioned through the access port, wherein the intermediate portion conforms to the surface of the surgical instrument positioned through the opening and forms the seal between the inner surface and the surgical instrument.

2. The device of claim 1, wherein the opening accommodates a wide range of instrument sizes.

3. The device of claim 1, wherein the access port is adapted to maintain a sealing relationship with a plurality of instruments positioned through the access port while accommodating relative movement between the plurality of instruments.

4. The device of claim 1, wherein the proximal flange diameter is equal to the distal flange diameter.

5. The device of claim 1, wherein the elastomeric material comprises a thermoplastic elastomer.

6. The device of claim 1, wherein the elastomeric material comprises a triblock copolymer.

7. The device of claim 1, wherein the elastomeric material comprises a foaming agent.

8. The device of claim 1, wherein the access port has a single opening.

9. The device of claim 1, wherein the access port is adapted to form a seal with a trocar positioned through the access port.

10. The device of claim 1, comprising a trocar configured for placement through a further opening in the access port.

11. The device of claim 1, further comprising an insufflation device adapted to deliver insufflation gas to the abdominal cavity to pressurize the abdominal cavity with the insufflation gas.

12. A surgical access device, comprising:
a non-inflatable access port sized to span a thickness of an abdominal wall of a patient and adapted to permit access of at least one surgical instrument through an incision in the abdominal wall of the patient and into an abdominal cavity, wherein the access port comprises a proximal portion, a distal portion, and an intermediate portion between the proximal portion and the distal portion, wherein an opening extends through the access port between the proximal portion and the distal portion, and
a surgical instrument, wherein the surgical instrument is a trocar having a valve structure configured to inhibit the escape of gas through the trocar when in use in an operative position,
wherein the proximal portion comprises a proximal flange having a proximal flange diameter, wherein the proximal portion has a proximal surface portion and a distal surface portion, wherein the proximal surface portion at least partially defines a concave area,
wherein the distal portion comprises a distal flange having a distal flange diameter,
wherein the proximal flange, the distal flange, and the intermediate portion are monolithically formed of an elastomeric material, wherein the intermediate portion comprises an outer surface and at least one inner surface, the outer surface has a diameter that is less than the proximal and distal flange diameters, the inner surface at least partially defines the opening, wherein the elastomeric material of the intermediate portion extends between the outer surface and the at least one inner surface, wherein the elastomeric material comprises a thermoplastic elastomer, and
wherein disposition of the access port within the abdominal wall maintains the access port in an operative position with the intermediate portion exerting a force on the incision forming a seal between the elastomeric material and the abdominal wall when positioned within the incision with the proximal flange disposed exteriorly of the abdominal wall and the distal flange disposed interiorly of the abdominal wall, and wherein the access port is adapted to form a seal with the surgical instrument positioned through the access port, wherein the elastomeric material conforms to the surface of the surgical instrument positioned through the opening and forms the seal within the intermediate portion between the proximal flange and the distal flange.

13. The device of claim 12, wherein the thermoplastic elastomer comprises a triblock copolymer.

14. The device of claim 13, wherein the triblock copolymer comprises Styrene-Ethylene/Butylene-Styrene.

15. The device of claim 13, wherein the thermoplastic elastomer comprises an oil.

16. The device of claim 15, wherein the thermoplastic elastomer comprises a foaming agent.

17. The device of claim 12, wherein the opening is configured to self seal in the absence of any instrument extending through the opening.

18. The device of claim 12, wherein the proximal surface portion has a proximal surface area, and the distal portion comprises a distal surface portion having a distal surface area less than the proximal surface area.

19. The device of claim 16, wherein a second instrument is configured for placement through a second opening in the access port.

20. The device of claim 12, further comprising an insufflation device adapted to deliver insufflation gas to the abdominal cavity to pressurize the abdominal cavity with the insufflation gas.

21. A surgical access device, comprising:
a non-inflatable access port and an instrument, wherein the access port is sized to span a thickness of an abdominal wall of a patient and adapted to permit access of the instrument through an opening in the patient and into a body cavity, wherein the access port comprises a proximal portion, a distal portion, and an intermediate portion between the proximal portion and the distal portion, wherein a channel extends through the access port between the proximal portion and the distal portion,
wherein the proximal portion comprises a proximal flange having a proximal flange diameter, wherein the proximal portion has a proximal surface portion having a proximal surface area, wherein at least a portion of the proximal surface area defines a concave area,
wherein the distal portion comprises a distal flange having a distal flange diameter, wherein the distal portion has a distal surface portion having a distal surface area,
wherein the proximal flange, the distal flange, and the intermediate portion are monolithically formed of an elastomeric material, wherein the intermediate portion comprises an outer surface and an inner surface, the outer surface has a diameter that is less than the proximal and distal flange diameters, the inner surface at least partially defines the channel,
wherein the access port is configured to be positioned within the opening in the patient with the intermediate portion disposed across the opening with the proximal flange disposed exteriorly of the opening and the distal flange disposed interiorly of the opening, wherein disposition of the intermediate portion within the opening provides a compressive force between the access port and the opening, and the instrument is a trocar configured to be positioned through the channel of the access port, wherein the trocar has a valve structure configured to inhibit the escape of gas through the trocar when in use in an operative position, wherein the intermediate portion is adapted to provide a seal with the surface of the instrument.

22. The device of claim 21, wherein the distal surface area is less than the proximal surface area.

23. The device of claim 21, further comprising an insufflation device adapted to deliver insufflation gas to the body cavity to pressurize the body cavity with the insufflation gas.

* * * * *